United States Patent
Chandraratna et al.

(10) Patent No.: US 7,105,566 B2
(45) Date of Patent: Sep. 12, 2006

(54) METHODS OF TREATMENT DURING VASCULAR PROCEDURES

(75) Inventors: Roshantha A. Chandraratna, Laguna Hills, CA (US); Yang-Dar Yuan, Irvine, CA (US); Tuong P. Dang, Lake Forest, CA (US); Sheng Z. Loh, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 349 days.

(21) Appl. No.: 10/278,770

(22) Filed: Oct. 22, 2002

(65) Prior Publication Data

US 2004/0077710 A1    Apr. 22, 2004

(51) Int. Cl.
*A61K 31/385*    (2006.01)
*A61K 31/38*    (2006.01)

(52) U.S. Cl. ..................... 514/434; 514/432
(58) Field of Classification Search ................ 514/434, 514/432
See application file for complete search history.

(56) References Cited

U.S. PATENT DOCUMENTS

| | | | | |
|---|---|---|---|---|
| 5,776,699 | A * | 7/1998 | Klein et al. ................. | 435/7.2 |
| 5,877,207 | A | 3/1999 | Klein et al. ................. | 514/456 |
| 5,919,970 | A | 7/1999 | Song et al. .................. | 560/48 |
| 5,958,954 | A | 9/1999 | Klein et al. ................. | 514/333 |
| 5,973,007 | A | 10/1999 | Demarchez et al. | |
| 6,037,488 | A | 3/2000 | Song et al. .................. | 560/52 |
| 6,133,309 | A * | 10/2000 | Bollag et al. ................ | 514/432 |
| 6,218,128 | B1 * | 4/2001 | Klein et al. ................. | 435/7.1 |
| 6,228,848 | B1 * | 5/2001 | Klein et al. ................. | 514/63 |
| 6,355,806 | B1 | 3/2002 | Johnson et al. | |
| 6,521,641 | B1 * | 2/2003 | Klein et al. ................. | 514/333 |
| 6,545,049 | B1 * | 4/2003 | Canan-Koch et al. ....... | 514/569 |
| 2002/0193403 | A1 * | 12/2002 | Yuan et al. ................. | 514/311 |
| 2005/0009868 | A1 * | 1/2005 | Underhill et al. ........... | 514/312 |

FOREIGN PATENT DOCUMENTS

| | | |
|---|---|---|
| WO | WO94/14777 | 7/1994 |
| WO | WO 99/33821 | 7/1999 |
| WO | WO 02/22113 | 3/2002 |

OTHER PUBLICATIONS

Fisher, Edwin., Effect of hypertension on cholesterol altherosclerosis in diabetic rabbits, (abstract only), Laboratory Investigation, (1961) vol. 10, pp. 361-372.*
Konneh et al., Red wine derived compounds and their putative antiatherogenic . . . , (abstract only), Colloques-Institut National de la Recherche Agronomique (1988), vol. 87(polyphenols 96), pp. 105-115.*

Kalinowski et al., Intra-arterial application of the ACE inhibitor ramipril using . . . , RoFO. Fortschritte auf dem Gebiete der Rontgenstrahlen und der Nuklearmedizin, (Nov. 1998) vol. 169(5), pp. 532-536.*
Johnson et al., Peripheral vascular complications of coronary angioplasty by . . . , (abstract only), Catheterization and cardiovascular diagnosis, (Mar. 1994), vol. 31(3), pp. 165-172.*
de Man et al., "Not acute but chronic hypertriglyceridemia is associated with impaired endothelium-dependent vasodilation: reversal after lipid-lowering therapy by atorvastin," *Arterioscerl. Thromb. Vasc. Biol.* 20:744-750 (2000).
Dol et al., "Simvastatin inhibits myointimal hyperplasia following carotid artery injury in cholesterol-fed rabbits," *Blood Coagulation Fibrinolysis* 7:772-778 (1996).
Hoogerbrugge et al., "Hypertriglyceridemia enhances monocyte binding to endothelial cells in NIDDM," *Diabetes Care* 19:1122-1125 (1996).
Horlein et al., "Ligand-independent repression by the thyroid hormone receptor mediated by a nuclear receptor co-repressor," *Nature* 277:397-404 (1995).
Klein et al., "Recruitment of nuclear receptor corepressor and coactivator to the retinoic acid receptor by retinoid ligands. Influence of DNA-heterodimer interactions," *J. Biol. Chem.* 275:19401-19408 (2000).
Kurokawa et al., "Regulation of retinoid signalling by receptor polarity and allosteric control of ligand binding," *Nature* 371:528-531 (1994).
Monti et al., "Triglycerides impair postischemic recovery in isolated hearts: roles of endothelin-1 and trimetazidine," *Am. J. Physiol. Heart Circ. Physiol.* 281:H1122-H1130 (2001).
Mouchon et al., "Allosteric regulation of the discriminative responsiveness of retinoic acid receptor to natural and synthetic ligands by retinoid X receptor and DNA," *Mol. Cell. Biol.* 19-3073-3085 (1999).
Mussoni et al., "Hypertriglyceridemia and regulation of fibrinolytic activity," *Arterioscler. Thrombosis* 12:19-27 (1992).
Rachez et al., "Ligand-dependent transcription activation by nuclear receptors requires the DRIP complex," *Nature* 398:824-828 (1999).
Shinohara et al., "Troglitazone suppresses intimal formation following balloon injury in insulin-resistant Zucker fatty rats," *Atherosclorsis* 136:275-279 (1998).
Thacher et al., "Therapeutic applications for ligands of retinoid receptors," *Current Pharm. Design* 6:25-58 (2000).
Whitfield et al., "Steroid hormone receptors: evolution, ligands and molecular basis of biologic function," *J. Cell. Biochem. Suppl.* 32/33:110-122 (1999).

* cited by examiner

*Primary Examiner*—Vickie Kim
(74) *Attorney, Agent, or Firm*—Hamilton, Brook, Smith & Reynolds, P.C.

(57) ABSTRACT

The invention provides in one embodiment a method for treating vascular trauma. The method can include administering to an individual undergoing vascular trauma an effective amount of a retinoic acid receptor (RAR) antagonist or an RAR inhibitor. The methods can be used to lower serum triglycerides in a patient undergoing an invasive vascular procedure such as vascular surgery.

16 Claims, 5 Drawing Sheets

METHODS OF TREATMENT DURING VASCULAR PROCEDURES

BACKGROUND OF THE INVENTION

1. Field of the Invention

The present invention relates generally to the field of medicine and, more specifically, to the field of treating cardiovascular disease.

2. Background Information

Coronary artery disease is the most common, serious, chronic, life-threatening illness in the United States, causing more deaths, disability and econonomic loss than many other illnesses. Atherosclerosis is a major cause of myocardial ischemia, which results in a lack of oxygen due to an imbalance between oxygen supply and demand.

Atherosclerosis is responsible for the majority of cases of myocardial and cerebral infarction and thus represents the principal cause of death in the United States and western Europe. Atherosclerosis refers to the thickened and hardened lesions of the medium and large muscular and elastic arteries. Atherosclerosis is characterized by lipid-rich lesions that occur within the innermost layer of the artery, the intima. The lesions are usually eccentric and, if they become sufficiently large, can occlude the artery and thus the vascular supply to a tissue or organ, resulting in ischemia or necrosis. If this occurs, it often leads to the characteristic clinical sequelae of myocardial infarction, cerebral infarction, gangrene of the extremities, or sudden cardiac death.

The two principal forms of atherosclerosis are the early lesion, or fatty streak, and the advanced lesion, or fibrous plaque, which can become an advanced complicated lesion. The fatty streak is the most common and ubiquitous lesion of atherosclerosis. The lesions of atherosclerosis are confined principally to the intima. Initially, the fatty streak appears to contain two cell types, foam cells that consist of macrophages filled with lipids, and T lymphocytes. The macrophages are derived from blood-borne monocytes that are chemotactically attracted into the artery wall, where they develop into foam cells.

The fibrous plaque is also located in the intima and characteristically leads to the eccentric thickening of the artery that often results in an occluded lumen. The fibrous plaque is typically covered at its luminal aspect by a thickened cap of dense connective tissue containing a special form of flattened, pancake-shaped smooth muscle cell that has formed the dense collagenous matrix in which it is embedded. Beneath this cap, the lesion is highly cellular and contains large numbers of smooth muscle cells, some of which are full of lipid droplets. It also contains numerous macrphages, many of which take the form of foam cells, together with variable numbers of T lymphocytes. These collections of cells usually overlie a deeper area of necrotic foam cells and debris. This necrotic area sometimes becomes calcified and often contains cholesterol crystals.

Risk factors for atherosclerosis include hypercholesterolemia, hypertension, cigarette smoking, obesity, as well as other factors. Atherosclerotic disease can be treated by life-style changes such as modified diet, exercise and stopping cigarette smoking. A variety of drug regimens can also be used, for example, to reduce cholesterol levels or blood pressure.

Despite the availability of drug and life-style interventions that modify risk factors for the development of atherosclerosis, a large number of individuals develop ischemic heart disease. Many patients who develop ischemic heart disease are improved by coronary revascularization procedures such as coronary artery bypass grafting or angioplasty. In the case of coronary artery bypass grafting, the method is effective in relieving symptoms, can achieve complete revascularization and is widely applicable. Disadvantages of coronary bypass surgery include high cost, increased risk of the need to repeat the procedure due to late graft closure, and morbidity.

Angioplasty provides the advantage of being less invasive, requiring a shorter hospital stay, having lower initial costs, and being effective in relieving symptoms. Disadvantages of angioplasty include restenosis, high incidence of incomplete revascularization, and uncertain long-term outcome. Restenosis occurs in about 30–45% of cases within 6 months of the angioplastic procedure.

More than 400,000 angioplastic procedures are performed in the United States each year. Therefore, the high recurrence of stenosis (restenosis) means that a significant number of patients must undergo follow up procedures, including repeated angioplasty.

Thus, there exists a need to improve the outcome of invasive vascular procedures such as angioplasty. The present invention satisfies this need, and provides related advantages as well.

SUMMARY OF THE INVENTION

The invention provides in one embodiment a method for treating vascular trauma. The method can include administering to an individual undergoing vascular trauma an effective amount of a retinoic acid receptor (RAR) antagonist or an RAR inhibitor. The methods can be used to lower serum triglycerides in a patient undergoing an invasive vascular procedure such as vascular surgery.

BRIEF DESCRIPTION OF THE DRAWINGS

FIG. 2 shows the effect of Compound 1 on triglyceride and cholesterol levels in female ZDF rats. Female ZDF rats were treated with control (corn oil) or various concentrations of Compound 1 (0.03, 0.1 and 0.3 mg/kg).

FIG. 3 shows the effect of Compound 1 and Compound 2 administered at a dose of 10 mg/kg on famale ZDF rats.

DETAILED DESCRIPTION OF THE INVENTION

Figure 1:
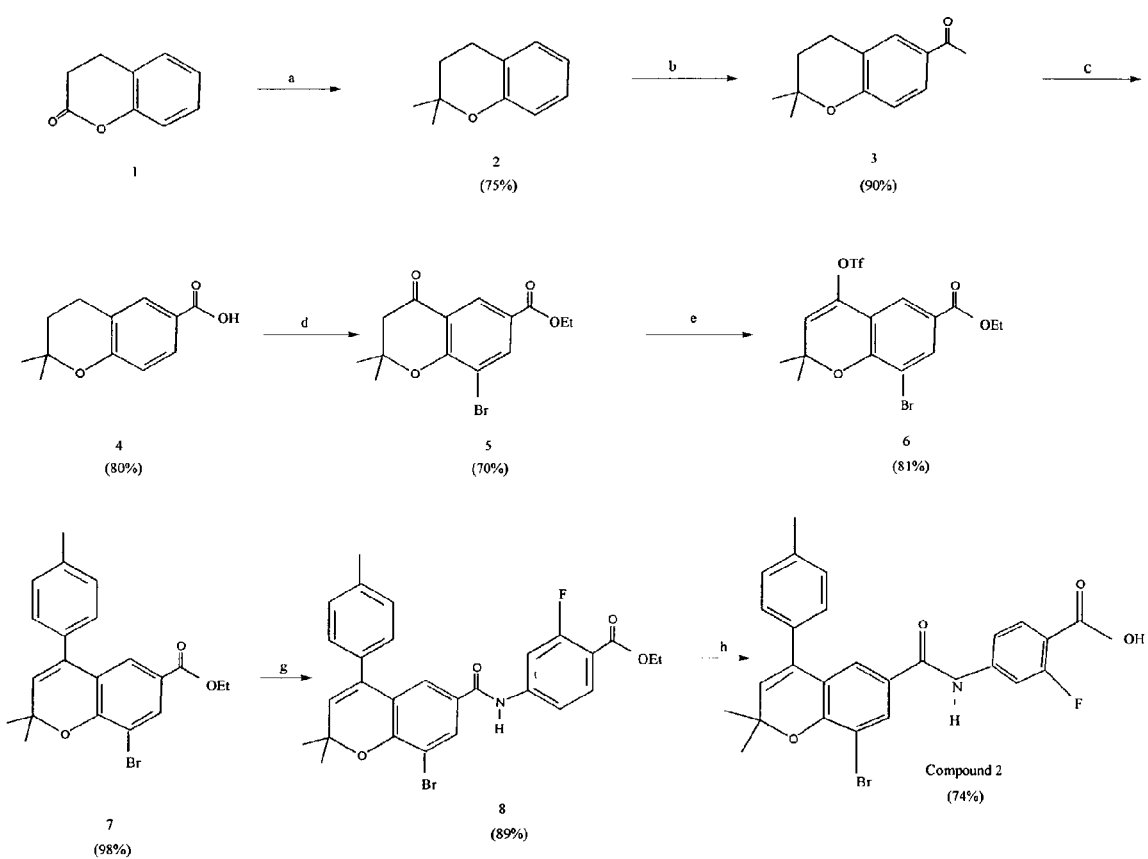
FIG. 1 shows an exemplary synthetic scheme for the synthesis of Compound 2.

The present invention provides a method for treating vascular trauma by administering to an individual undergoing vascular trauma an effective amount of a retinoic acid receptor (RAR) antagonist or an RAR inhibitor. The methods of the invention are useful for facilitating patient recovery from an invasive vascular procedure such as angioplasty. An RAR antagonist or RAR inhibitor is administered prior to and after vascular surgery, and the administration of an RAR antagonist or RAR inhibitor enhances the recovery of the patient from the surgical procedure.

Administration of RAR antagonists, inhibitors, or inverse agonists reduces serum triglycerides, thereby ameliorating adverse effects of elevated triglycerides and effecting enhanced recovery of patients undergoing invasive vascular procedures. Hypertriglyceridemia can affect vascular function in various ways. High triglycerides are known to impair myocardial recovery after low-flow ischemia (Monti et al., Am. J. Physiol. Heart Circ. Physiol. 281:H1122–H1130 (2001)). Hypertriglyceridemia is also known to enhance monocyte binding to endothelial cells (Hoogerbrugge et al., Diabetes Care 19:1122–1125 (1996)). Since the recruitment of monocytes occurs during the development of atherosclerotic lesions, the enhancement of monocyte binding during hypertriglyceridemia can be a factor in the development of atherosclerotic lesions. Hypertriglyceridemic patients have been shown to have higher plasminogen activator inhibitor-1, which hinders the fibrinolytic system (Mussoni et al., Arterioscler. Thrombosis 12:19–27 (1992)). Furthermore, impaired endothelium-dependent vasodilation has been observed in patients with chronic hypertriglyceridemia. In methods of the invention, RAR antagonists, inhibitors or inverse agonists are administered, resulting in a decrease in triglyceride levels, thereby reducing undesirable biological effects associated with hypertriglyceridemia. The methods can thus be used to maintain vascular integrity, avoid post-surgical complications and prevent or reduce the recurrence of vascular obstruction such as restenosis.

The methods of the invention can be used to treat a patient undergoing cardiovascular surgery and thereby benefit the patient by lowering serum triglycerides. The methods can be used to lower serum triglycerides to normal or even below normal levels. In one embodiment, the methods of the invention can be used to enhance wound healing or normal re-epithelialization. In another embodiment, the methods of the invention can be used in a vascular procedure such as angioplasty to decrease or prevent post-operational complications such as clot formation or restenosis. For example, an RAR antagonist can be used to enhance wound healing or decrease post-operational complications associated with a surgical procedure.

The invention provides in one embodiment a method for treating vascular trauma by administering to an individual undergoing vascular trauma an effective amount of a retinoic acid receptor (RAR) antagonist, inhibitor, or inverse agonist. Retinoids exert their biological effects through one or both of two families of nuclear hormone receptors, retinoic acid receptors (RARs) and retinoid X receptors (RXRs). Retinoic acid receptors and retinoid X receptors are ligand-dependent transcription factors which regulate gene transcription by both upregulating gene expression through binding RA-responsive elements and down-regulating gene expression by antagonizing the enhancer action of other transcription factors such as AP1. Distinct RXRα, RXRβ and RXRγ isotypes and RARα, RARβ and RARγ isotypes are encoded by separate genes. Both RXR and RAR isotypes can be further expressed as several isoforms. RAR isoforms differ in the N-terminal A region; these isoforms are generated by alternative splicing or differential usage of two promoters. Like other nuclear hormone receptors, RAR and RXR receptors in their native form are localized at least in part to the nucleus and contain DNA-binding, and ligand binding domains.

Nucleic acid sequences encoding human and other mammalian, vertebrate and non-vertebrate retinoic acid receptors readily can be obtained from a variety of sources, for example, from databases such as GenBank. Exemplary RARs include, for example, a nucleic acid sequence encoding human RARα, which is available as GenBank accession AF088890; a nucleic acid sequence encoding human RARβ, which is available as GenBank accession NM_000965; and a nucleic acid sequence encoding human RARγ, which is available, for example, as GenBank accession M38258.

As used herein, a "retinoic acid receptor antagonist" or "RAR antagonist" refers to a chemical compound and/or complexes of compounds having binding activity for the retinoic acid binding site of RAR. An RAR antagonist blocks the binding of retinoic acid to the receptor and thereby prevents or inhibits RAR activation. An RAR antagonist can be readily determined using routine binding assays measuring competetive binding for retinoic acid to RAR.

As used herein, an "inverse agonist" is a chemical compound and/or complexes of compounds which is able to suppress the basal level of a retinoid receptor, for example an RAR, activity. Such activity can include homo- or heterodimerization and transacting transcriptional control of various genes whose regulation is normally responsive to RAR modulation.

As used herein, an "RAR inhibitor" refers to a compound that reduces RAR expression, activity or intracellular signaling in the presence or absence of ligand. Such an inhibitor can be, for example, a small molecule, protein, peptide, peptidomimetic, ribozyme, nucleic acid molecule or oligonucleotide, oligosaccharide, or combination thereof. An RAR inhibitor can include, for example, an antagonist; an inverse agonist; a dominant negative molecule that prevents RAR activation; antibodies, proteins, small molecules and oligonucleotides that prevent or diminish ligand binding to RAR; ribozymes, antisense nucleic acid molecules, and nucleic acid molecules encoding negative regulatory transcription factors that prevent or reduce RAR expression, as well as cells or viruses containing such ribozymes and nucleic acid molecules, and selective inhibitors of RAR intracellular signaling. One skilled in the art will readily understand that these and other molecules that inhibit RAR expression, activity or signaling can be used as an RAR inhibitor. An RAR inhibitor includes an RAR antagonist and an RAR inverse agonist since such molecules can inhibit RAR activity.

A dominant negative molecule that prevents RAR activation refers to a variant of a wild type RAR that acts to reduce activity of wild type RAR. While it is recognized that a dominant negative receptor can function through a variety of mechanisms, exemplary mechanisms through which a dominant negative RAR can function include, without limitation, depletion of free ligand and formation of inactive wild type/dominant negative receptor dimers.

A sequence-specific ribonuclease such as a ribozyme or an antisense nucleic acid molecule can also be used to inhibit the expression of RAR. A sequence-specific ribonuclease refers to a molecule that catalyzes the cleavage of RNA at a defined ribonucleotide sequence. A ribozyme refers to an RNA molecule that catalyzes the cleavage of RNA at a defined ribonucleotide sequence. Ribozymes such as hammerheads and hairpins can be designed and prepared by routine methods. The specificity of ribozymes such as hammerheads and hairpins for a target cleavage site is determined by base-pairing between the ribozyme and its RNA target. Methods of designing ribozymes are well known as described, for example, in Hauswirth and Lewin, *Prog. Retin. Eye Res.* 19:689–710 (2000), and Lewin and Hauswirth, *Trends. Mol. Med.* 7:221–228 (2001).

Sequence-specific ribonucleases, including ribozymes and DNA enzymes, can be designed as described above and prepared by standard methods for synthesis of nucleic acid molecules. See, also, Ke et al., *Int. J. Oncol.* 12:1391–1396 (1998); Doherty et al., *Ann. Rev. Biophys. Biomol. Struct.* 30:457–475 (2001); Hauswirth and Lewin, supra, 2000; and Lewin and Hauswirth, supra, 2001. Sequence-specific ribozymes also can be identified by in vitro selection from pools of random sequences. Such methods are well-established, as described, for example, in Bartel and Szostak, *Science* 261:1411–1418 (1993), Breaker, *Chem. Rev.* 97:371–390 (1997) and Santoro and Joyce, *Proc. Natl. Acad. Sci., USA* 94:4262–4266 (1997)).

Where a ribozyme is to be administered to a patient without being delivered using a viral or other vector, the ribozyme can be modified, if desired, to enhance stability. Modifications useful in a therapeutic ribozyme include, but are not limited to, blocking the 3' end of the molecule and the 2' positions of pyrimidines. Stabilized ribozymes can have half-lives of hours and can be administered repeatedly using, for example, intravenous or topical injection. Those skilled in the art understand that a ribozyme also can be administered by expression in a viral gene therapy vector. A DNA oligonucleotide encoding the ribozyme can be cloned downstream of a RNA pol II or RNA pol III promoter and, if desired, can be embedded within the transcripts of genes such as tRNAval, U6 snRNA or the adenoviral VA1 RNA.

An antisense nucleic acid molecule refers to a nucleic acid molecule that is complementary in sequence to all or part of a molecule of messenger RNA or another specific RNA transcript. An antisense nucleic acid molecule can be, for example, DNA or RNA, and can include naturally occurring nucleotides as well as synthetic nucleotides or other non-naturally occurring modifications such as modifications to the phosphate backbone that improve stability. Antisense oligonucleotides, including phosphorothioate and other modified oligonucleotides, are encompassed by the term antisense nucleic acid molecule as used herein. Without being bound by the following, an antisense nucleic acid molecule useful in the invention can reduce mRNA translation or increase mRNA degradation, thereby reducing expression of the target mRNA.

The homology requirement for reduction of expression using antisense methodology can be determined empirically. Generally, at least about 80–90% nucleic acid sequence identity is present in an antisense nucleic acid molecule useful in the invention, with higher nucleic acid sequence identity often used in antisense oligonucleotides, which can be perfectly identical to the patient's endogenous transcript. The target sequence can be chosen, if desired, to have a small single-stranded region at which nucleation takes place, in addition to a double-stranded, helically ordered stem that is invaded by the antisense molecule to displace one of the strands (Mir and Southern, *Nature Biotech.* 17:788–792 (1999). Methods for selecting and preparing antisense nucleic acid molecules are well known in the art and include in silico approaches (Patzel et al. *Nucl. Acids Res.* 27:4328–4334 (1999); Cheng et al., *Proc. Natl. Acad. Sci., USA* 93:8502–8507 (1996); Lebedeva and Stein, *Ann. Rev. Pharmacol. Toxicol.* 41:403–419 (2001); Juliano and Yoo, *Curr. Opin. Mol. Ther.* 2:297–303 (2000); and Cho-Chung, *Pharmacol. Ther.* 82:437–449 (1999)).

As used herein, the term "pan," when used in reference to an RAR antagonist, RAR inhibitor, or RAR inverse agonist, refers to an RAR compound that binds to all forms of RAR, for example, RARα, RARβ and RARγ. A pan RAR antagonist, inhibitor or inverse agonist can exhibit differential binding between the forms of RAR so long as the pan RAR antagonist, inhibitor or inverse agonist binds to each RAR form such as RARα, RARβ and RARγ.

As used herein, the term "selective," when used in reference to an RAR antagonist, inhibitor or inverse agonist, refers to a compound that exhibits differential inhibitory activity between one form of RAR over at least one other form of RAR. For example, a selective RAR antagonist can bind to RARα and RARβ but not RARγ. Such an RAR antagonist is selective for RARα and RARβ. Similarly, an RAR antagonist selective for RARα and RARγ binds to these forms but not RARβ. An RAR inhibitor or inverse agonist that is not an RAR antagonist, that is, an inhibitor that decreases RAR activity but does not bind to the retinoic acid binding site of RAR, can be selective for inhibiting the activity of a subset of RAR forms, for example, selectively inhibiting the activity of RARα and RARβ but not RARγ. A selective RAR antagonist, inhibitor or inverse agonist can also be selective for a particular RAR form without significant binding or inhibitory activity to other subtypes, for example, selective for RARα but not RARβ or RARγ or selective for RARβ but not RARα or RARγ. Such an RAR antagonist is selective for RARα. It is understood that any single RAR form or combination of RAR forms can be applicable to a selective RAR antagonist, inhibitor, or inverse agonist, so long as the compound does not significantly inhibit activity of or bind to all of the RAR forms.

A selective RAR antagonist, inhibitor or inverse agonist has at least about 10-fold higher affinity and/or inhibitory activity for one RAR form compared to at least one other RAR form. For example, a selective RAR antagonist can have at least about 15-fold higher, about 20-fold higher, about 25-fold higher, about 30-fold higher, about 35-fold higher, about 40-fold higher, about 45-fold higher, about 50-fold higher, about 60-fold higher, about 70-fold higher, about 80-fold higher, or about 90-fold higher binding activity or even higher for one RAR form compared to another. A selective RAR inhibitor or inverse agonist can exhibit similar higher fold inhibitory activity as that recited above for an RAR antagonist.

A specific RAR antagonist, inhibitor or inverse agonist has at least about 100-fold higher affinity and/or activity for one RAR form compared to at least one other RAR form. A specific RAR antagonist can have have at least about 150-fold higher, about 200-fold higher, about 250-fold higher, about 300-fold higher, about 400-fold higher, about 500-fold higher, about 600-fold higher, about 700-fold higher, about 800-fold higher, about 900-fold higher, or about 1000-fold higher or even higher binding activity for one RAR form over at least one other RAR form. A specific RAR inhibitor or inverse agonist can exhibit similar fold higher inhibitory activity as that recited above for an RAR antagonist.

Thus, in one embodiment, the invention provides methods using a pan RAR antagonist, inhibitor or inverse agonist. In another embodiment, the invention additionally provides methods using a selective RAR antagonist, inhibitor or inverse agonist. For example, the RAR antagonist, inhibitor or inverse agonist can be selective for RARα and/or RARβ.

The methods of the invention involve the administration of an RAR antagonist, RAR inhibitor or RAR inverse agonist. Any of a number of RAR antagonists, inhibitors or inverse agonists can be used in methods of the invention, as disclosed herein.

Some examples of structures and methods of making and using retinoid receptor antagonists and/or inverse agonists, for example RAR antagonists or inverse agonists, are provided in U.S. Pat. Nos. 5,776,699; 5,958,954; 5,877,207; 5,919,970, and U.S. application Ser. No. 09/848,159, each of which is incorporated by reference herein in their entirety.

A class of compounds of the invention has the structure:

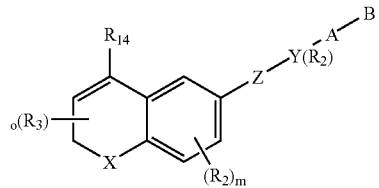

wherein X is S, O, NR' where R' is H or alkyl of 1 to 6 carbons, or

X is $[C(R_1)_2]_n$ where $R_1$ is independently H or alkyl of 1 to 6 carbons, and n is an integer between, and including, 0 and 2, and;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons, and;

$R_3$ is hydrogen, lower alkyl of 1 to 6 carbons or F, and;

m is an integer having the value of 0–3, and;

o is an integer having the value of 0–3, and;

Z is —C≡C—,
—N═N—,
—N═$CR_1$—,
—$CR_1$═N,
—($CR_1$═$CR_1$)$_{n'}$— where n' is an integer having the value 0–5,
—CO—$NR_1$—,
—CS—$NR_1$—,
—$NR_1$—CO,
—$NR_1$—CS,
—COO—,
—OCO—;
—CSO—;
—OCS—;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —($CR_1$═$CR_1$)$_{n'}$— and n' is 3, 4 or 5 then Y represents a direct valence bond between said $(CR_2$═$CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–5, and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons.

Another class of compounds of the invention has the structure:

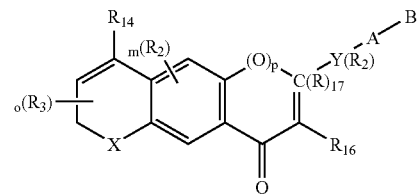

wherein X is S, O, NR' where R' is H or alkyl of 1 to 6 carbons, or

X is $[C(R_1)_2]_n$, where $R_1$ is independently H or alkyl of 1 to 6 carbons, and n is an integer between, and including, 0 and 2, and;

$R_2$ is independently hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons, and;

$R_3$ independently is hydrogen, lower alkyl of 1 to 6 carbons or F, and;

m is an integer having the value of 0, 1, 2, or 3, and;

o is an integer having the value of 0, 1, 2, or 3, and;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, and;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and;

$R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0, 1, 2, 3, 4 or 5, and;

$R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons, and;

$R_{16}$ is H, lower alkyl of 1 to 6 carbons, and;

$R_{17}$ is H, lower alkyl of 1 to 6 carbons, OH or $OCOR_{11}$, and;

p is 0 or 1, with the proviso that when p is 1 then there is no $R_{17}$ substituent group, and m is an integer between, and including, 0 and 2.

A further class of compounds of the invention is the class of the structure:

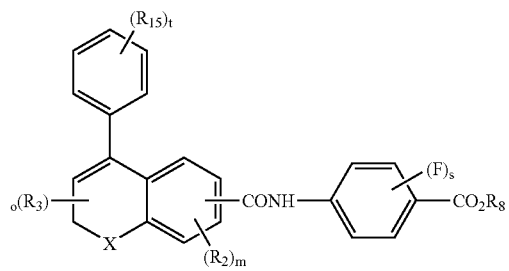

where X is $C(R_1)_2$ or O, and;

$R_1$ is H or alkyl of 1 to 6 carbons, and;

$R_2$ is lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons, and;

m is an integer having the value of 0–3, and;

$R_3$ is lower alkyl of 1 to 6 carbons of F, and;

o is an integer having the value of 0–3, and;

s is an integer having the value of 1–3, and;

$R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, and;

$R_{15}$ is independently H, F, Cl, Br, I, $NO_2$, $N(R_8)_2$, $COR_8$, $NR_8CON(R_8)_2$, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, an alkynyl group having 1 to 10 carbons and 1 to 3 triple bonds, or a trialkylsilyl or trialkylsilyloxy group where the alkyl groups independently have 1 to 6 carbons, and;

t is an integer having the values of 0, 1, 2, 3, 4, or 5, and;

the CONH group is in the 6 or 7 position of the benzopyran, and in the 2 or 3 position of the dihydronaphthaline ring, or a pharmaceutically acceptable salt of said compound.

Another class of compounds is that of the structure:

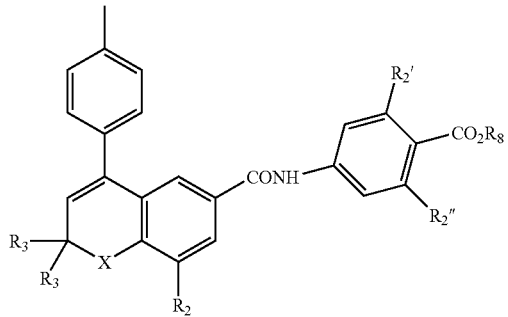

where X is $C(CH_3)_2$ or O, and;

$R_2$ is H or Br, and;

$R_2'$ and $R_2''$ independently are H or F, and;

$R_3$ is H or $CH_3$, and;

$R_8$ is H, lower alkyl of 1 to 6 carbons, or a pharmaceutically acceptable salt of said compound.

A further class of such compounds has the structure:

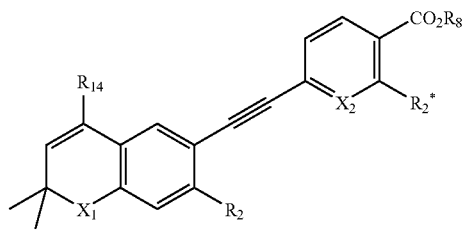

where $X_1$ is S or O;

$X_2$ is CH or N;

$R_2$ is H, F, $CF_3$ or alkoxy of 1 to 6 carbons;

$R_2*$ is H, F, or $CF_3$;

$R_8$ is H, or lower alkyl of 1 to 6 carbons;

$R_{14}$ is unsubstituted phenyl, thienyl or pyridyl, or phenyl, thienyl or pyridyl substituted with one to three $R_{15}$ groups, where $R_{15}$ is lower alkyl of 1 to 6 carbons, chlorine, $CF_3$, or alkoxy of 1 to 6 carbons, or a pharmaceutically acceptable salt of said compound.

In yet another embodiment of the invention, the compound has the structure:

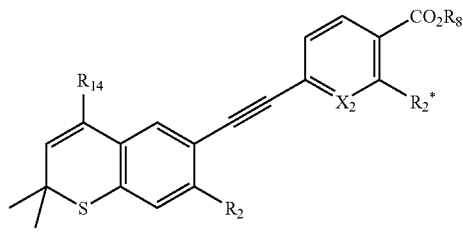

wherein $X_2$ is CH or N, and;

$R_2$ is H, F, or $OCH_3$, and;

$R_2*$ is H or F, and;

$R_8$ is H, or lower alkyl of 1 to 6 carbons, and;

$R_{14}$ is selected from the group consisting of phenyl, 4-(lower-alkyl)phenyl, 5-(lower alkyl)-2-thienyl, and 6-(lower alkyl)-3-pyridyl where lower alkyl has 1 to 6 carbons, or a pharmaceutically acceptable salt of said compound.

Another class of compounds for use in an embodiment of the present invention has the following structure:

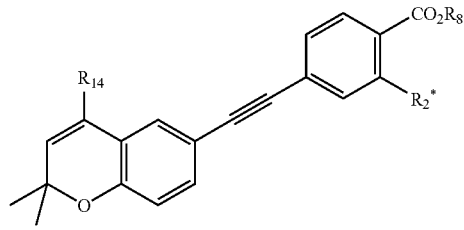

where $R_2*$ is H or F;

$R_8$ is H, or lower alkyl of 1 to 6 carbons, and $R_{14}$ is selected from the group consisting of phenyl, and 4-(lower-alkyl)phenyl, where lower alkyl has 1 to 6 carbons, or a pharmaceutically acceptable salt of said compound.

Another compound class has the following structure:

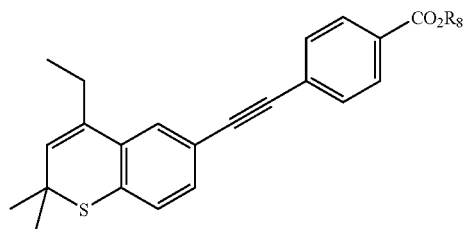

where $R_8$ is H, lower alkyl of 1 to 6 carbons, or a pharmaceutically acceptable salt of said compound.

Yet another compound is one having the following structure:

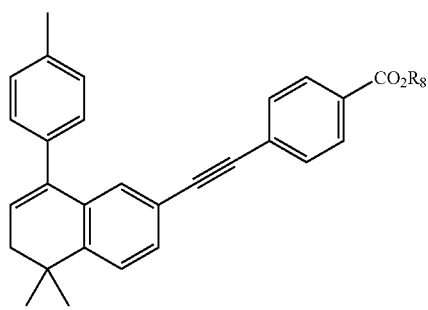

where $R_8$ is H, lower alkyl of 1 to 6 carbons, or a pharmaceutically acceptable salt of said compound. When $R_8$ is H, this compound is termed Compound 4.

Yet another class of compounds contemplated for use in the present invention is that having the structure:

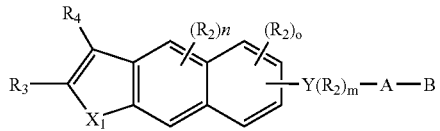

wherein $X_1$ is: —$C(R_1)_2$—, —$C(R_1)_2$—$C(R_1)_2$—, —S—, —O—, —$NR_1$—, —$C(R_1)_2$—O—, —$C(R_1)_2$—S—, or —$C(R_1)_2$—$NR_1$—; and $R_1$ is independently H or alkyl of 1 to 6 carbons; and $R_2$ is optional and is defined as lower alkyl of 1 to 6 carbons, F, Cl, Br, I, $CF_3$, fluoro substituted alkyl of 1 to 6 carbons, OH SH, alkoxy of 1 to 6 carbons, or alkylthio of 1 to 6 carbons; and m is an integer between, and including, 0 and 4; and n is an integer between, and including, 0 and 2; and o is an integer between, and including, 0 and 3; and $R_3$ is H, lower alkyl of 1 to 6 carbons, F, Cl, Br or I; and $R_4$ is $(R_5)_p$-phenyl, $(R_5)_p$-naphthyl, $(R_5)_p$-heteroaryl where the heteroaryl group is five-membered or 6-membered and has 1 to 3 heteroatoms selected from the group consisting of O, S, and N; and p is an integer between, and including, 0 and 5; and $R_5$ is optional and is defined as independently F, Cl, Br, I, $NO_2$, $N(R_8)_2$, $N(R_8)COR_8$, $N(R_8)CON(R_8)_2$, OH, $OCOR_8$, $OR_8$, CN, COOH, $COOR_8$, an alkyl group having from 1 to 10 carbons, an alkenyl group having from 1 to 10 carbons and 1 to three double bonds, alkynyl group having from 1 to 10 carbons and 1 to 3 triple bonds, or a (trialkyl)silyl or (trialkyl)silyloxy group where the alkyl groups independently have from 1 to 6 carbons; and Y is a phenyl or naphthyl group, or a heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or Y is —$(CR_3=CR_3)_r$—; and r is an integer between, and including, 1 and 3; and A is $(CH_2)_q$ where q is an integer from 0–5, lower branched chain alkyl having from 3 to 6 carbons, cycloalkyl having from 3 to 6 carbons, alkenyl having from 2 to 6 carbons and 1 or 2 double bonds, alkenyl having from 2 to 6 carbons and 1 or 2 triple bonds, with the proviso that when Y is —$(CR_3=CR_3)_r$— then A is $(CH_2)_q$ and q is 0; and B is H, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, wherein $R_7$ is an alkyl, cycloalkyl or alkenyl group containing 1 to 5 carbons, $R_8$ is an alkyl group of 1 to 10 carbons or (trimethylsilyl)alkyl, where the alkyl group has 1 to 10 carbons, or a cycloalkyl group of 5 to 10 carbons, or $R_8$ is phenyl or lower alkylphenyl, $R_9$ and $R_{10}$ independently are H, a lower alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is a divalent alkyl radical of 2–5 carbons. A non-exclusive list of compounds falling within this description, and methods for making this class of compounds are disclosed in U.S. Pat. No. 5,728,846 to Vuligonda et al., the disclosure of which is hereby incorporated by reference as part of this application.

Also useful in the present invention are compounds of the formula:

Y₃(R₄)—X—Y₁(R₁R₂)-Z-Y₂(R₂)-A-B where Y₁ is phenyl, naphthyl, or heteroaryl selected from the group consisting of pyridyl, thienyl, furyl, pyridazinyl, pyrimidinyl, pyrazinyl, thiazonyl, ozazolyl, imidazolyl, and pyrrazolyl, said phenyl, naphthyl, and heteroaryl groups being substituted with an $R_1$ group, and further substituted or unsubstituted with one or two $R_2$ groups;

$R_1$ is $C_{1-10}$ alkyl, 1-ademantyl, 2-tetrahydropyranoxy, trialkylsilanyloxy where alkyl has up to 6 carbons, OH, alkoxy where the alkyl group has up to 10 carbons, alkylthio where the alkyl group has up to 10 carbons, or $OCH_2OC_{1-6}$ alkyl;

$R_2$ is lower alkyl of 1 to 6 carbons, F, Cl, Br, I, $CF_3$, $CF_2CF_3$, OH, $OR_3$, $NO_2$, $N(R_3)_2$, CN, $N_3$, $COR_3$, $NHCOR_3$, COOH, or $COOR_3$;

X is $(C(R_3)_2$, S, SO, $SO_2$, O or $NR_3$;

Z is —C≡C—,
—N=N—,
—N(O)=N—,
—N=N(O)—,
—N=CR₃—,
—CR₃=N,
—(CR₃=CR₃)ₙ— where n is an integer having the value 0–5,
—CO—NR₃—,
—CS—NR₃—,
—NR₃—CO,
—NR₃—CS,
—COO—,
—OCO—;
—CSO—;
—OCS—; or
—CO—CR₃=R₃—O, $R_3$ is independently H or lower alkyl of 1 to 6 carbons;

Y₂ is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one or two $R_2$ groups, or when Z is —(CR₃=CR₃)ₙ— and n is 3, 4 or 5 then Y₂ represents a direct valence bond between said —(CR₃=CR₃)ₙ group and B;

Y₃ is phenyl, naphthyl, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one to three $R_4$ groups, where $R_4$ is alkyl of 1 to 10 carbons, fluoro-substituted alkyl of 1 to 10 carbons, alkenyl of 2 to 10 carbons and having 1 to 3 triple bonds, F, Cl, Br, I, $NO_2$, CN, $NR_3$, $N_3$, COOH, $COOC_{1-6}$ alkyl, OH, SH, $OC_{1-6}$ alkyl, and $SC_{1-6}$ alkyl;

A is $(CH_2)_q$ where q is from 0–5, lower branched alkyl having 3–6 carbons, cycloalkyl having 3–6 carbons, alkenyl, having 2–6 carbons and 1–2 double bonds, alkynyl having 2–6 carbons and 1 to 2 triple bonds, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}$ alkyl$)_3$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound. These compounds are disclosed in U.S. Pat. No. 5,919,970 to Song et al., which is incorporated by reference herein in its entirety.

Additional RAR antagonists or inverse agonists are described in U.S. Pat. No. 6,037,488, to Song and Chandraratna, which is incorporated by reference herein in its entirety. Also, compounds useful in the methods of the present invention are disclosed in International Application Publication No. WO 94/14777, to Yoshimura et al., which is also incorporated by reference herein in its entirety. This latter application discloses RAR antagonists.

Furthermore, the structures of additional compounds useful in the present invention are disclosed below.

A.

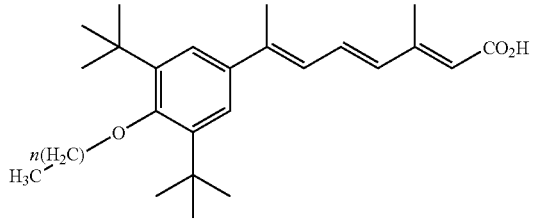

where n is an integer from 1 to 10.

B.

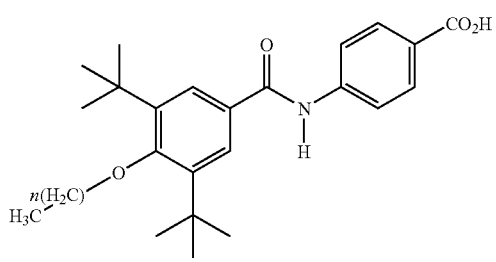

where n is an integer from 1 to 10.

C.

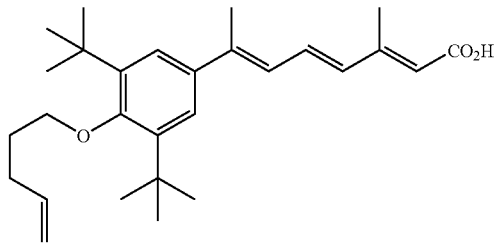

-continued

D.

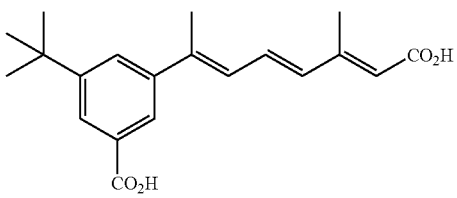

E.

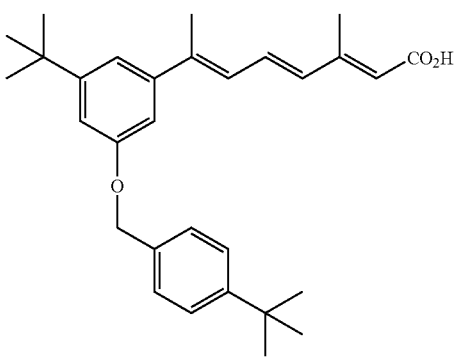

Additional exemplary RAR antagonists, inhibitors or inverse agonists include Compound 1, Compound 2 and Compound 3, as disclosed in the Examples.

Compound 1 has the structure shown below and is an exemplary pan RAR antagonist. An exemplary synthesis of Compound 1 is described in Example I.

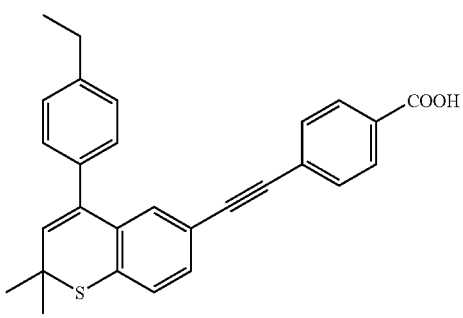

Compound 2 has the structure shown below and is an exmplary selective RAR antagonist, selective for RARα. An exemplary synthesis is described in Example II.

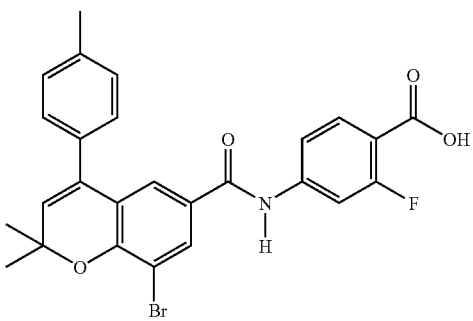

A useful subgroup of RAR antagonists, inhibitors or inverse agonists is the set of those RAR antagonists or inverse agonists that lack antagonist, inhibitor or inverse agonist activity at one or more subclasses of RARs, such as the RARα, RARβ, or RARγ receptors. Such a selective RAR antagonist, inhibitor or inverse agonist exhibits "subclass-specific" activity and can result in the minimization of toxicity of the drug. Such compounds can have activity for only on RAR receptor such as the RARα, RARβ, or RARγ receptors, or at any combination of these, so long as the combination is less than all of the receptors. A compound having antagonist, inhibitor or inverse agonist activity for all of the RAR receptors is considered a pan-RAR antagonist, inhibitor or inverse agonist. Determination of whether a compound has subclass-specific inverse agonist activity can be performed using translational screening as disclosed in U.S. Pat. No. 6,218,128, to Klein et al., and Ser. No. 09/108,298, to Nagpal et al., both of which are incorporated by reference herein in their entirety. An RAR antagonist can be determined, for example, by testing for competitive binding with retinoic acid to an RAR using well known competitive binding assays.

The compounds disclosed herein clearly suggest the synthesis and use of other compounds structurally similar to these, for use in the methods of the present invention. In addition to the compounds referred to herein, other compounds that have PAR antagonist and/or inverse agonist activity are also expected to lower the level of lipid, in particular triglycerol, and thus be useful in treating vascular trauma, for example, angioplasty or other invasive vascular procedures.

Exemplary methods of synthesis of an PAR antagonist, inhibitor or inverse agonist are described in Examples I and II. Other exemplary methods of synthesis of RAR antagonists, inhibitors or inverse agonists are described in U.S. Pat. Nos. 6,218,128; 6,037,488; 5,919,970; 5,877,207 and 5,958,954 and WO 94/14777. These and other PAR antagonists, inhibitors or inverse agonists can be readily prepared by one skilled in the art in the same manner as that disclosed herein using well known methods of chemical synthesis, including methods similar to those exemplified herein (see Examples I and II).

The methods of the invention can be used to improve patient outcome and facilitate the recovery of a patient undergoing vascular surgery. The methods of the invention can thus be used to treat a vascular trauma. As used herein, "vascular trauma" refers to an invasive vascular procedure in which the integrity of a vessel is disrupted. Vascular trauma thus can include vascular surgery, including cardiovascular surgery. Cardiovascular surgery can include procedures such as bypass surgery or angioplasty. In the case of bypass surgery or angioplasty, such vascular procedures are performed intentionally. Vascular trauma can also include an accidental trauma in which the vasculature is injured or damaged. Thus, is another embodiment, the invention provides a method for facilitating wound healing in a patient. Such methods can decrease the recovery time or otherwise facilitate the healing of a wound. The wound can be from an accident or the result of a surgical procedure.

The methods of the invention are particularly useful for enhancing recovery from angioplasty since the methods of the invention reduce triglyceride levels. The reduction of triglycerides suppresses undesirable biological effects of high triglycerides, thus providing the patient with the benefit of enhanced recovery. Thus, the methods can be particularly useful in patients having high triglycerides, since such patients are more susceptible to the adverse consequences of high triglycerides before and after the surgical procedure.

The methods of the invention can thus be applied to a number of angioplastic procedures. Such angioplastic procudures include, for example, the use of stents, balloon angioplasty, laser angioplasty, atherectomy catheters, and the like. Modification of such procedures are included, for example, the use of drug-coated stents to prevent restenosis. Because angioplasty results in up to 40% occurrence of restenosis, the methods of the invention are applicable to a large number of individuals and can be used to inhibit restenosis, thus improving the recovery of patients undergoing such procedures. In still another embodiment of the invention, the invention provides a method of ameliorating an adverse reaction to angioplasty such as restenosis. The methods can thus be used to reduce the time and/or severity of onset of restenosis.

The methods of the invention can also be applied in combination with other forms of therapy that facilitate the recovery of a patient from vascular surgery. For example, a variety of drugs are generally provided to a patient before and after surgery to enhance the patient's recovery. It has been shown that lipid-lowering agents such as atorvastatin is able to reverse the impaired vasodilation associated with chronic hypertriglyceridemic patients (de Man et al., *Arterioscerl. Thromb. Vasc. Biol.* 20:744–750 (2000)). Simvistatin has also been shown to inhibit myointimal hyperplasia following carotid artery injury in cholesterol fed rabbits (Dol et al., *Blood Coagulation Fibrinolysis* 7:772–778 (1996)). Other lipid-lowering agents such as troglitazone are also capable of suppressing intimal formation following balloon injury in a Zucker fatty rat model (Shinohara et al., *Atherosclorsis* 136:275–279 (1998)).

The invention thus provides in another embodiment methods where a second lipid lowering agent is adminstered to an individual in addition to an RAR antagonist, inhibitor or inverse agonist. For example, a statin can be administered as a second lipid lowering agent. Exemplary statins include, but are not limited to, lovastatin, pravastatin, simvastatin, cerivastatin, fluvastatin, atorvastatin and mevastatin. A thiazolidinedione can also be administered as a second lipid lowering agent. Exemplary thiazolidinediones include, but are not limited to, troglitazone, pioglitazone and ciglitazone.

For therapeutic applications in accordance with the present invention the RAR antagonist, RAR inhibitor RAR or inverse agonist compounds can be incorporated into pharmaceutical compositions, such as tablets, pills, capsules, solutions, suspensions, creams, ointments, gels, salves, lotions and the like, using such pharmaceutically acceptable excipients and vehicles which are well known in the art. For example, preparation of various formulations such as topical formulations are well described in Remington's Pharmaceutical Science, Edition 17, Mack Publishing Company, Easton, Pa; incorporated by reference herein. For topical application, the RAR antagonist, inhibitor or inverse agonist compounds can also be administered as a powder or spray, particularly in aerosol form. If the RAR antagonist, inhibitor or inverse agonist is to be administered systemically, it can be prepared as a powder, pill, tablet or the like or as a syrup or elixir suitable for oral administration. For intravenous or intraperitoneal administration, the RAR antagonist, inhibitor or inverse agonist can be prepared as a solution or suspension capable of being administered by injection. In certain cases, it can be useful to formulate the antagonist, inhibitor or inverse agonist compounds in a solution for injection. In other cases, it can be useful to formulate the antagonist, inhibitor or inverse agonist compounds in suppository form or as extended release formulation for deposit under the skin or intramuscular injection.

The antagonist, inhibitor or inverse agonist compounds are administered in a therapeutically effective dose in accordance with the invention. A therapeutic concentration is that concentration which is effective to lower the concentration of lipids, for example triglycerol, in a mammal, for example, a human being. A particularly useful formulation generally contains between about 0.1 and about 3 mg of an RAR antagonist, inhibitor or inverse agonist/kg of body weight, for example, between about 0.3 mg/kg and 2 mg/kg, and particularly between about 0.7 mg/kg and about 1.5 mg/kg will constitute a therapeutically effective concentration for oral application, with routine experimentation providing adjustments to these concentrations for other routes of administration if necessary. One skilled in the art can readily determine an effective does by administering a dose and measuring the level of triglycerides compared to a control, for example, the individual prior to treatment. The dosage can be adjusted accordingly based on a desire to modulate triglyceride levels after treatment.

In a further embodiment, a pharmaceutical composition comprising the RAR antagonist, inhibitor or inverse agonist is administered orally. Such composition can be in the form of a liquid, syrup, suspension, tablet, capsule, or gelatin-coated formulation. In another embodiment, a pharmaceutical composition comprising an RAR antagonist, inhibitor or inverse agonist is topically administered. Such a composition can be in the form of a patch, cream, lotion, emulsion, or gel. In yet another embodiment, a pharmaceutical composition comprising the RAR antagonist, inhibitor or inverse agonist can be inhaled. Such composition can be formulated as an inhalant, suppository or nasal spray.

An RAR antagonist, inhibitor or inverse agonist is administered at an effective amount to lower serum triglycerides. In particular, the methods of the invention can be used to lower serum triglycerides by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90% relative to pre-treatment levels. In one embodiment, the methods of the invention can be used to lower serum triglyceride levels at least about 20% relative to pre-treatment levels, for example, a pre-treatment level of about 100 mg/dl lowered to about 80 mg/dl would be at least about a 20% reduction in serum triglyceride levels relative to pre-treatment levels. In another embodiment, the methods of the invention can be used to lower serum triglyceride levels at least about 20% to at least about 50% relative to pre-treatment levels.

As used herein, administering to an individual "undergoing" vascular trauma can include administering an RAR antagonist, inhibitor or inverse agonist before, during and/or after vascular trauma, for example, before, during and/or after a planned surgical procedure. It is understood that one skilled in the art can readily determine an appropriate time before, during, and/or after a surgical procedure to administer an RAR antagonist, inhibitor or inverse agonist to effect a desired lowering of serum triglycerides.

An RAR antagonist, inhibitor or inverse agonist can be administered prior to a planned surgical procedure so that serum triglycerides are lowered in advance of the procedure. Generally, an RAR antagonist, inhibitor or inverse agonist is administered at least about 1 day prior to surgery, for example, at least about 2 days prior, at least about 3 days prior, at least about 4 days prior, at least about 5 days prior, at least about 6 days prior, or at least about 7 days prior or even longer prior to surgery, if desired, for example, at least about 10 days, at least about 12 days, or at least about 14 days prior to the procedure. Generally, an RAR antagonist, inhibitor or inverse agonist is administered at least about 3 to about 7 days prior to an invasive vascular surgical procedure. An RAR antagonist, inhibitor or inverse agonist can be administered a sufficient amount of time in advance of surgery to lower serum triglycerides to a desired level prior to the surgical procedure. One skilled in the art can readily determine a suitable time in advance of a planned surgical procedure for administration of an RAR antagonist, inhibitor, or inverse agonist.

An RAR antagonist, inhibitor or inverse agonist also can be administered after a surgical procedure so that serum triglycerides are continued to be lowered immediately following and during recovery from the surgical procedure. Generally, an RAR antagonist, inhibitor or inverse agonist is administered for at least about 1 day after surgery, for example, at least about 2 days after, at least about 3 days after, at least about 4 days after, at least about 5 days after, at least about 6 days after, at least about 7 days after, at least about 8 days after, at least about 9 days after, at least about 10 days after, at least about 11 days after, at least about 12 days after, at least about 13 days after, or at least about 14 days after, or even longer. In general, an RAR antagonist, inhibitor or inverse agonist is adminstered for at least about 7 to about 14 days after an invasive surgical procedure. One skilled in the art can readily determine a suitable time to continue administering an RAR antagonist, inhibitor, or inverse agonist after a surgical procedure.

The following examples are intended to illustrate but not limit the present invention.

EXAMPLE I

Synthesis of Compound 1

Compound 1 has the following chemical structure:

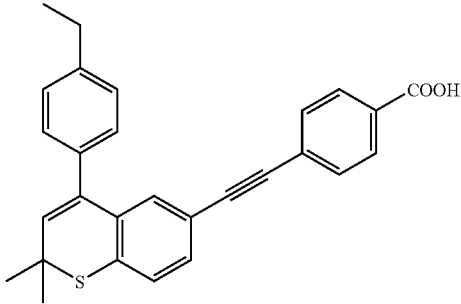

Compound 1, 4-[[4-(4-ethylphenyl)-2,2-dimethyl-(2H)-thiochromen-6-yl]-ethynyl]-benzoic acid, can be synthesized using conventional organic synthetic methods. A method for synthesizing Compound 1 is described below.

Step 1: A heavy-walled screw cap tube was charged with 3-methyl-2-butenoic acid (13.86 g, 138.4 mmol), 4-methoxy thiophenol (20.0 g, 138.4 mmol), and piperidine (3.45 g, 41.6 mmol). This mixture was heated to 105° C. for 32 hours, cooled to room temperature and dissolved in ethyl acetate (EtOAc) (700mL). The resulting solution was washed with 1M aqueous HCl, $H_2O$, and saturated aqueous NaCl before being dried over $Na_2SO_4$. Concentration of the dry solution under reduced pressure afforded an oil which, upon standing in the freezer, provided a crystalline solid. 3-(4-methoxy-phenylsulfanyl)-3-methyl-butyric acid was isolated as pale-yellow crystals by washing the crystalline solid with pentane. (27.33 g, 82%). $^1H$ NMR (300 MHz, $CDCl_3$) δ: 7.48 (2H, d, J=9.0 Hz), 6.89 (2H, d, J=8.9 Hz), 3.83 (3H, s), 2.54 (2H, s), 1.40 (6H, s).

Step 2: To a solution of 3-(4-methoxy-phenylsulfanyl)-3-methyl-butyric acid (20.0 g, 83.2 mmol) in 250 mL of benzene at room temperature was added a solution of oxalyl chloride (15.84 g, 124.8 mmol) in 10 mL of benzene over 30 minutes. After 4 hours, the solution was washed with ice cold 5% aqueous NaOH (a large volume of gas is released during this procedure), followed by ice cold $H_2O$, and finally saturated aqueous NaCl. The solution was dried ($Na_2SO_4$) and concentrated under reduced pressure to give a clear yellow oil. This material was used without further purification in the next step. $^1H$ NMR (300 MHz, $CDCl_3$) δ: 7.45 (2H, d, J=8.8 Hz), 6.90 (2H, d, J=8.8 Hz), 3.84 (3H, s), 3.12 (2H, s), 1.41 (6H, s).

Step 3: To a solution of the acyl chloride product of Step 2 (21.5 g, 83.2 mmol) in 250 mL of $CH_2Cl_2$ at 0° C. was added dropwise to a solution of $SnCl_4$ (21.7 g, 83.2 mmol) in 30 mL of $CH_2Cl_2$. After 2 hours, the reaction was quenched by slow addition of 150 mL $H_2O$. The organic layer was washed with 1M aqueous HCl, 5% aqueous NaOH, $H_2O$, and finally saturated aqueous NaCl before being dried over $MgSO_4$. Concentration under reduced pressure and vacuum distillation of the residual oil (Bulb-to-bulb, 125–135° C., 5 mm/Hg) afforded 14.48 g (78%) of 6-methoxy-2,2-dimethyl-thiochroman-4-one as a pale-yellow oil. $^1H$ NMR (300 MHz, $CDCl_3$) δ: 7.62 (1H, d, J=2.9 Hz), 7.14 (1H, d, J=8.6 Hz), 7.03 (1H, dd, J=2.8, 8.3 Hz), 3.83 (3H, s), 2.87 (2H, s), 1.46 (6H, s).

Step 4: To a solution of 6-methoxy-2,2dimethylthiochroman-4-one (6.0 g, 27 mmol) in 50 mL $CH_2Cl_2$ cooled to −23° C. was added $BBr_3$ (20.0 g, 80.0 mmol; 80.0 mL of a 1M solution in $CH_2Cl_2$) over a 20 minute period. After stirring for 5 hours at −23° C. the solution was cooled to −78° C. and quenched by the slow addition of 50 mL of $H_2O$. Upon warming to room temperature, the aqueous layer was extracted with $CH_2Cl_2$ and the combined organic layers were washed with saturated aqueous $NaHCO_3$, $H_2O$, and saturated aqueous NaCl before being dried over $MgSO_4$. Removal of the solvents under reduced pressure gave a green-brown solid which upon recrystalization (diethyl ether ($Et_2O$)/hexanes) afforded 2.25 g (40%) of 6-hydroxy-2,2-dimethylthiochroman-4-one as a light brown solid. $^1H$ NMR (300 MHz, $CDCl_3$) δ:7.63 (1H, d, J=2.8 Hz), 7.15 (1H, d, J=8.5 Hz), 7.01 (1H, dd, J=2.8, 8.5 Hz), 2.87 (2H, s), 1.46 (6H, s).

Step 5: To a solution of 6-hydroxy-2,2dimethylthiochroman-4-one (165.0 mg, 0.79 mmol) in 5.0 mL of anhydrous pyridine at 0° C. was added trifluoromethanesulfonic anhydride (245.0 mg, 0.87 mmol). After 4 hours at 0° C. the solution was concentrated and the residual oil dissolved in $Et_2O$, washed with $H_2O$ followed by saturated aqueous NaCl, and dried over $MgSO_4$. Removal of the solvents under reduced pressure and column chromatography (5% EtOAc/hexanes) afforded 126.0 mg (47%) of 2,2-Dimethyl-4-oxo-thiochroman-6-yl trifluoromethanesulfonate as a colorless solid. $^1H$ NMR (300 MHz, $CDCl_3$) δ: 7.97 (1H, s), 7.32 (2H, s), 2.90 (2H, s), 1.49 (6H, s).

Step 6: A solution of 2,2-dimethyl-4-oxothiochroman-6-yl trifluoromethanesulfonate (2.88 g, 8.50 mmol) in 10 mL triethylamine ($Et_3N$) and 20.0 mL dimethylformamide (DMF) was sparged with argon for 10 minutes. To this solution was added trimethylsilylacetylene (4.15 g, 42.0 mmol) and bis(triphenylphosphine)-palladium(II) chloride (298.0 mg, 0.425 mmol). The solution was heated to 95° C. for 5 hours, cooled to room temperature, and diluted with H$_2$O. Extraction with EtOAc was followed by washing the combined organic layers with H$_2$O and saturated aqueous NaCl and drying over MgSO$_4$. Concentration of the dry solution under reduced pressure and isolation of the product by column chromatography (3% EtOAc/hexanes) afforded 2.23 g (91%) of the 2,2-dimethyl-6-trimethylsilanylethynyl-thiochroman-4-one as an orange oil. $^1$H NMR (300 MHz, CDCl$_3$) δ: 8.18 (1H, d, J=1.9 Hz), 7.34 (1H, dd, J=1.9, 8.1 Hz), 7.15 (1H, d, J=8.1 Hz), 2.85 (2H, s), 1.45 (6H, s), 0.23 (9H, s).

Step 7: A solution of 2,2-dimethyl-6-trimethylsilanylethynyl-thiochroman-4-one (110.0 mg, 0.38 mmol) and K$_2$CO$_3$ (40.0 mg, 0.29 mmol) in 10.0 mL MeOH was stirred overnight at room temperature. The solution was diluted with H$_2$O and extracted with Et$_2$O. The combined organic layers were washed with H$_2$O and saturated aqueous NaCl and dried over MgSO$_4$. Removal of the solvent under reduced pressure afforded 81 mg (99%) of the 6-ethynyl-2,2-dimethylthiochroman-4-one as an orange oil. $^1$H NMR (300 MHz, CDCl$_3$) δ:8.20 (1H, d, J=1.9 Hz), 7.46 (1H, dd, J=1.9, 8.1 Hz), 7.18 (1H, d, J=8.1 Hz), 3.08 (1H, s), 2.86 (2H, s), 1.46 (6H, s).

Step 8: A solution of 6-ethynyl-2,2-dimethylthiochroman-4-one (82.0 mg, 0.38 mmol) and ethyl 4-iodobenzoate (104.9 mg, 0.38 mmol) in 5.0 mL Et$_3$N was purged with argon for 10 minutes. To this solution were added bis(triphenylphosphine)-palladium(II) chloride (88.0 mg, 0.12 mmol) and copper(I) iodide (22.9 mg, 0.12 mmol). After sparging for an additional 5 minutes with argon, the solution was stirred overnight at room temperature. The reaction mixture was filtered through a pad of Celite using an Et$_2$O wash. Concentration of the filtrate under reduced pressure, followed by column chromatography of the residual solid, afforded 100 mg (72%) of ethyl 4-[(2,2-dimethyl-4-oxo-thiochroman-6-yl)ethynyl]-benzoate as a yellow solid. $^1$H NMR (300 MHz, CDCl$_3$) δ: 8.25 (1H, d, J=1.8 Hz), 8.00 (2H, d, J=8.4 Hz), 7.55 (2H, d, J=8.4 Hz), 7.53 (1H, dd, J=1.8, 8.2 Hz), 7.21 (1H, d, J=8.2 Hz), 4.37 (2H, q, J=7.1 Hz), 2.88 (2H, s), 1.47 (6H, s), 1.39 (3H, t, J=7.1 Hz).

Step 9: A solution of sodium bis(trimethylsilyl)amide (1.12 g, 6.13 mmol) in 16.2 mL of tetrahydrofuran (THF) was cooled to −78° C. and a solution of ethyl 4-(2,2-dimethyl-4-oxo-thiochroman-6-ylethynyl)-benzoate (1.86g, 5.10 mmol) in 15.0 mL was added slowly. After 30 minutes, a solution of 2-[N,N-bis(trifluoromethanesulfonyl)amino]-5-pyridine (2.40 g, 6.13 mmol) in 10 mL of THF was added. After 5 minutes, the solution was warmed to room temperature and stirred overnight. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. Ethyl 4-((2,2-dimethyl-4-trifluoromethanesulfonyloxy-(2H)-thiochromen-6-yl)ethynyl)-benzoate, 1.53 g (61%), was isolated by column chromatography (2% EtOAc/hexanes) as a yellow solid. $^1$H NMR (300 MHz, CDCl$_3$) δ: 8.03 (2H, d, J=8.4 Hz), 7.61 (1H, d, J=1.8 Hz), 7.59 (2H, d, J=8.4 Hz), 7.41 (1H, dd, J=1.8, 8.1Hz), 7.29 (1H, d, J=8.1 Hz), 5.91 (1H, s), 4.39 (2H, q, J=7.1 Hz), 1.53 (6H, s), 1.41 (3H, t, J=7.1 Hz).

Step 10: A solution of 4-ethylbromobenzene (670.9 mg, 3.63 mmol) in 4.0 mL of THF was cooled to −78° C. and tert-butyllithium (464.5 mg, 7.25 mmol, 4.26 mL of a 1.7M solution in pentane) was added to give a yellow solution. After 30 minutes, a solution of ZnCl$_2$ (658.7 mg, 4.83 mmol) in 8.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-benzoate (1.20 g, 2.42 mmol) and tetrakis(triphenylphosphine)palladium(0) (111.7 mg, 0.097 mmol) in 8.0 mL THF. This solution was heated to 50° C. for 1 hour, cooled to room temperature, and the reaction quenched by the addition of saturated aqueous NH$_4$Cl. The solution was extracted with EtOAc and the combined organic layers were washed with H$_2$O and saturated aqueous NaCl before being dried (MgSO$_4$) and concentrated under reduced pressure. Ethyl 4-[[4-(4-ethylphenyl)-2,2-dimethyl-(2H)-thiochromen-6-yl]-ethynyl]-benzoate was isolated by column chromatography (5% EtOAc/hexanes) as a colorless oil.

$^1$H NMR (300 MHz, CDCl$_3$) δ: 7.99 (2H, d, J=8.2 Hz), 7.52 (2H, d, J=8.4 Hz), 7.40 (5H, m), 7.35 (2H, m), 5.85 (1H, s), 4.38 (2H, q, J=7.1 Hz), 2.72 (2H, q, J=7.6 Hz), 1.48 (6H, s), 1.40 (3H, t, J=7.1 Hz), 1.30 (3H, t, J=7.6 Hz).

Step 11: To a solution of ethyl 4-[[4-(4-ethylphenyl)-2,2-dimethyl-(2H)-thiochromen-6-yl]-ethynyl]-benzoate (940.0 mg, 2.08 mmol) in 10.0 mL THF and 5.0 mL ethanol (EtOH) was added NaOH (416.0 mg, 10.4 mmol, 5.2 mL of a 2M aqueous solution). The resulting solution was stirred overnight at room temperature. The reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 786.0 mg (89%) of 4[[4-(4-ethylphenyl)-2,2-dimethyl-(2H)-thiochromen-6-yl]-ethynyl]-benzoic acid as a colorless solid. $^1$H NMR (300 MHz, d$_6$-acetone) δ: 8.01 (2H, d, J=8.3 Hz), 7.60 (2H, d, J=8.5 Hz), 7.42 (2H, m), 7.29 (2H, m), 7.22 (3H, m), 5.94 (1H, s), 2.69 (2H, q, J=7.7 Hz), 1.47 (6H, s), 1.25 (3H, t, J=7.7 Hz). This compound, the final desired product, was termed Compound 1.

In some cases, Compound 1 was provided as follows: the compound was dissolved in capric/caprylic triglyceride (CCT) at a variety of doses, either 0.001% (v/v) Compound 1, 0.003% (v/v) Compound 1, or 0.01% (v/v) Compound 1. Control animals received the CCT vehicle without the Compound 1 active ingredient (Compound 1 Vehicle). In other experiments, Compound 1 was dissolved in vehicle (2% dimethylsulfoxide (DMSO), 98% corn oil). Although many retinoids and retinoid analogs are light labile, this compound is relatively stable to normal light.

EXAMPLE II

Synthesis of Compound 2

This example describes the synthesis of Compound 2. Compound 2 can be synthesized using conventional organic synthesis methods. A method for synthesizing Compound 2 is described below.

A synthetic scheme for the synthesis of Compound 2 is shown in FIG. 1. Briefly, commercially available dihydrocoumarin (structure 1 in FIG. 1) was first treated with Grignard reagent (step a: (i) MeMgBr, ether, 0° C.; (ii) conc. H$_2$SO$_4$) to give chroman 2. Chroman 2 was acetylated (step b: AcCl, AlCl$_3$, CH$_2$Cl$_2$, 0° C.) under Friedel-Craft's condition to give ketone 3. Oxidation of ketone 3 with NaOBr (step c: NaOBr, dioxane/H$_2$O) afforded acid 4. Acid 4 was further converted to ester 5 via esterification, bromination and CrO$_3$ oxidation (step d: (i) EtOH, conc. H$_2$SO$_4$, reflux; (ii) Br$_2$, HOAc; (iii) CrO$_3$, Ac$_2$O, HOAc).

Ester 5 was treated with triflic anhydride and pyridine (step e: Tf$_2$O, pyridine, CH$_2$Cl$_2$, reflux) to derive triflate 6. Triflate 6 was reacted with p-tolylboronic acid under Suzuki's condition (step f: p-tolylboronic acid, Pd(PPH$_3$)$_4$, Na$_2$CO$_{3(aq)}$, LiCl, toluene, MeOH, 95° C.) to yield ester 7. The product, Compound 2, was derived from ester 7 through hydrolysis, coupling with aminobenzoate (step g: (i) KOH, EtOH, reflux, (ii) oxalyl chloride, CH$_2$Cl$_2$, 0° C. to r.t. (iii) methyl 4-amino-2-fluorobenzoate, pyridine, 60° C.) and saponification (step h: KOH, MeOH, reflux).

The composition of Compound 2 is C$_{26}$H$_{21}$BrFNO$_4$; mass 509.06, molecular weight 510.35 (C,61.19; H, 4.15; Br, 15.66; F, 3.72; N, 2.74 and O 12.54).

EXAMPLE III

Treatment of ZDF Rats with an RAR Antagonist/Inhibitor

This example describes the effect of RAR antagonists/inhibitors on triglyceride and cholesterol levels in female ZDF rats.

ZDF rats, which are hyperlipidemic and diabetic, were used as a model to test the effect of RAR antagonists/inhibitors on serum lipids. Female ZDF rats (10–11 weeks old) were fed a GMI 13004 diet, a diabetogenic, high fat diet, for 5–6 weeks. Compound 1 was dissolved in vehicle (2% DMSO, 98% corn oil). Compound 1 was administered at a dosage of 0.03 mg/kg, 0.1 mg/kg, and 0.3 mg/kg body weight. Dosings were performed at approximately 8 a.m. Serum was collected at approximately 12 p.m. on the day before dosing (Day 0, 4 hour); the third day of dosing (Day 3, 4 hour); the seventh day of dosing (Day 7, 4 hour); and 24 hours after the last dosing (Day 8, 0 hour). The levels of triglycerides and cholesterol in the serum samples were measured. The results are shown in Table 1 and are illustrated graphically in FIGS. 2A and 2B.

TABLE 1

Effect of RAR antagonist Compound 1 on serum triglyceride and cholesterol of female ZDF rats fed a diabetogenic high fat diet.

| Oral | No. | Triglycerides | | | | Cholesterol | | | |
|---|---|---|---|---|---|---|---|---|---|
| | | day 0, 4 hr | day 3, 4 hr | day 7, 4 hr | day 8, 0 hr | day 0, 4 hr | day 3, 4 hr | day 7, 4 hr | day 8, 0 hr |
| | 1 | 1233 | 1275 | 1245 | 1446 | 156 | 138 | 129 | 141 |
| Corn oil | 2 | 1191 | 1047 | 1107 | 1314 | 111 | 111 | 105 | 126 |
| | 3 | 1170 | 1323 | 1098 | 1380 | 114 | 138 | 135 | 141 |
| | 4 | 1314 | 1551 | 1413 | 1416 | 135 | 147 | 147 | 153 |
| Mean | | 1227 | 1299 | 1216 | 1389 | 129 | 134 | 129 | 140 |
| SD | | 64 | 207 | 148 | 57 | 21 | 16 | 18 | 11 |
| | 5 | 1200 | 663 | 771 | 846 | 114 | 93 | 111 | 108 |
| Compound 1 | 6 | 1245 | 651 | 468 | 531 | 129 | 96 | 105 | 93 |
| 0.03 mg/kg | 7 | 1944 | 1197 | 855 | 1230 | 129 | 129 | 96 | 108 |
| | 8 | 945 | 666 | 903 | 516 | 120 | 102 | 123 | 129 |
| Mean | | 1334 | 794 | 749 | 781 | 123 | 105 | 109 | 110 |
| SD | | 428 | 269 | 195 | 336 | 7 | 16 | 11 | 15 |
| P vs. control | | 0.655 | 0.027 | 0.010 | 0.034 | 0.619 | 0.046 | 0.110 | 0.018 |
| | 9 | 1284 | 402 | 429 | 390 | 123 | 129 | 114 | 102 |
| Compound 1 | 10 | 993 | 360 | 384 | 339 | 123 | 84 | 90 | 105 |
| 0.1 mg/kg | 11 | 1197 | 681 | 618 | 486 | 129 | 96 | 111 | 102 |
| | 12 | 1356 | 546 | 588 | 699 | 126 | 114 | 111 | 111 |
| Mean | | 1208 | 497 | 505 | 479 | 125 | 106 | 107 | 105 |
| SD | | 157 | 146 | 116 | 159 | 3 | 20 | 11 | 4 |
| P vs. control | | 0.829 | 0.001 | 0.000 | 0.001 | 0.745 | 0.072 | 0.083 | 0.004 |
| | 13 | 882 | 282 | 195 | 222 | 105 | 93 | 99 | 102 |
| Compound 1 | 14 | 1725 | 234 | 222 | 180 | 141 | 96 | 126 | 120 |
| 0.3 mg/kg | 15 | 2244 | 297 | 267 | 195 | 156 | 108 | 132 | 123 |
| | 16 | 1350 | 315 | 174 | 261 | 123 | 108 | 120 | 114 |
| Mean | | 1550 | 282 | 215 | 215 | 131 | 101 | 119 | 115 |
| SD | | 577 | 35 | 40 | 36 | 22 | 8 | 14 | 9 |
| P vs. control | | 0.345 | 0.002 | 0.000 | 0.000 | 0.887 | 0.017 | 0.426 | 0.013 |

Figure 2A:
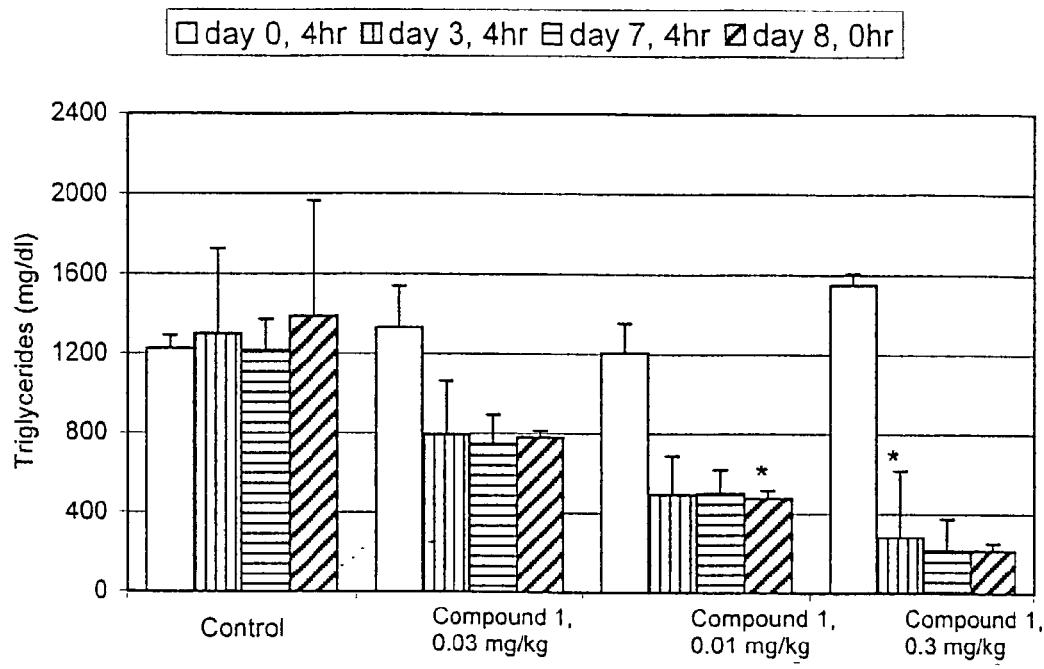
FIG. 2A shows the effect of Compound 1 on serum triglyceride levels in female ZDF rats fed a diabetogenic high fat diet.
Figure 2B:
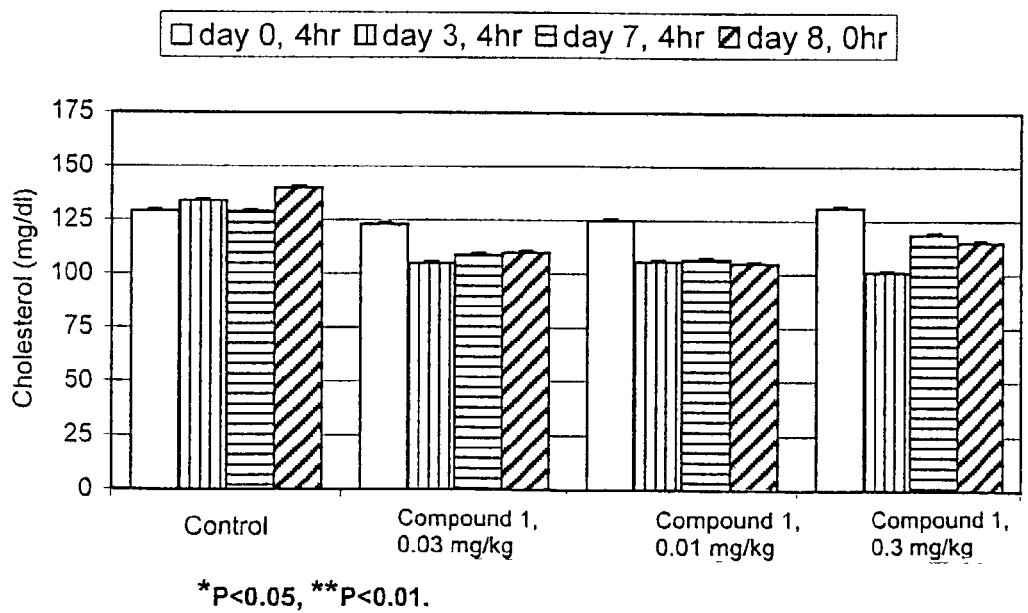
FIG. 2B shows the effect of Compound 1 on serum cholesterol levels in female ZDF rats fed a diabetogenic high fat diet.

As shown in Table 1 and FIGS. 2A and 2B, Compound 1 as highly effective in lowering serum triglycerides in hyperlipidemic, diabetic ZDF rats. A does of Compound 1 at 0.03, 0.1 and 0.3 mg/kg resulted in serum triglyceride levels about 59%, 40%, and 14%, respectively, of pre-treatment triglyceride levels (see Table 1 FIG. 2A). The effect was observed by Day 3 of administration and was sustained throughout Day 8.

The effect of Compound 1 on serum cholesterol levels was also tested. Compound 1 was found to be effective at lowering serum cholesterol levels, although the effect was more modest than observed for serum triglycerides.

A similar experiment to that described above was performed. Briefly, female ZDF rats (12 weeks old) were fed either a PM 5008 diet or a GMI 13004 diet. Control vehicle consisted of 2% DMSO and 98% corn oil. Compound 1 and Compound 2 were administered at a dosage of 10 mg/kg body weight. Dosings were administered at approximately 8 a.m. Serum was collected on the first day of dosing at approximately 8 a.m. (Day 1, 0 hour) and 2 p.m. (Day 1, 6 hour); the fourth day of dosing at approximately 8 a.m. (Day 4, 0 hour); and the last day of dosing at approximately 8 a.m. (Day 7, 0 hour) and 2 p.m. (Day 7, 6 hour). The levels of triglycerides and cholesterol in the serum samples were measured. The results are shown in Table 2 and are illustrated graphically in FIGS. 3A and 3B.

TABLE 2

Effect of RAR antagonists Compound 2 and Compound 1 on serum triglyceride and cholesterol of female ZDF rats fed a diabetogenic high fat diet.

| Oral | No. | Triglycerides | | | | | Cholesterol | | | | |
|---|---|---|---|---|---|---|---|---|---|---|---|
| | | day 1, 0 hr | day 1, 6 hr | day 4, 0 hr | day 7, 0 hr | day 7, 6 hr | day 1, 0 hr | day 1, 6 hr | day 4, 0 hr | day 7, 0 hr | day 7, 6 hr |
| Corn oil | 5 | 1392 | 1578 | 1248 | 1572 | 1254 | 114 | 96 | 102 | 96 | 84 |
| | 6 | 1836 | 2190 | 1590 | 1134 | 1374 | 120 | 120 | 108 | 84 | 78 |
| | 7 | 1578 | 1626 | 1428 | 1896 | 1152 | 120 | 114 | 108 | 132 | 102 |
| | 8 | 1596 | 1458 | 1602 | 1734 | 1398 | 102 | 90 | 102 | 96 | 84 |
| | 9 | 2088 | 1608 | 1266 | 1884 | 1842 | 120 | 114 | 96 | 108 | 84 |
| | 10 | 1818 | 1620 | 1422 | 2052 | 1782 | 126 | 108 | 96 | 108 | 96 |
| Mean | | 1718 | 1680 | 1426 | 1712 | 1467 | 117 | 107 | 102 | 104 | 88 |
| SD | | 246 | 257 | 152 | 327 | 282 | 8 | 12 | 5 | 16 | 9 |
| Compound 2 10 mg/kg GMI 13004 diet | 17 | 1464 | 1260 | 642 | 294 | 402 | 120 | 114 | 84 | 78 | 72 |
| | 18 | 1194 | 1338 | 804 | 588 | 600 | 96 | 84 | 66 | 60 | 60 |
| | 19 | 1284 | 1140 | 210 | 474 | 360 | 96 | 90 | 72 | 54 | 54 |
| | 20 | 1668 | 1344 | 630 | 726 | 738 | 120 | 108 | 90 | 78 | 66 |
| | 21 | 1746 | 1524 | 570 | 720 | 912 | 162 | 132 | 72 | 60 | 60 |
| Mean | | 1471 | 1321 | 571 | 560 | 602 | 119 | 106 | 77 | 66 | 62 |
| SD | | 238 | 140 | 220 | 182 | 231 | 27 | 19 | 10 | 11 | 7 |
| Compound 1 10 mg/kg GMI 13004 diet | 23 | 1770 | 1248 | 174 | 78 | 96 | 162 | 132 | 78 | 96 | 102 |
| | 25 | 1182 | 750 | 132 | 96 | 66 | 108 | 90 | 90 | 84 | 72 |
| | 26 | 1500 | 1674 | 114 | 60 | 60 | 156 | 126 | 84 | 96 | 132 |
| | 27 | 1278 | 978 | 102 | 60 | 60 | 108 | 90 | 66 | 66 | 48 |
| | 28 | 1320 | 1266 | 168 | 66 | 150 | 120 | 96 | 90 | 102 | 96 |
| Mean | | 1410 | 1183 | 138 | 72 | 86 | 131 | 107 | 82 | 89 | 90 |
| SD | | 232 | 347 | 32 | 15 | 39 | 26 | 21 | 10 | 14 | 32 |

Figure 3A:
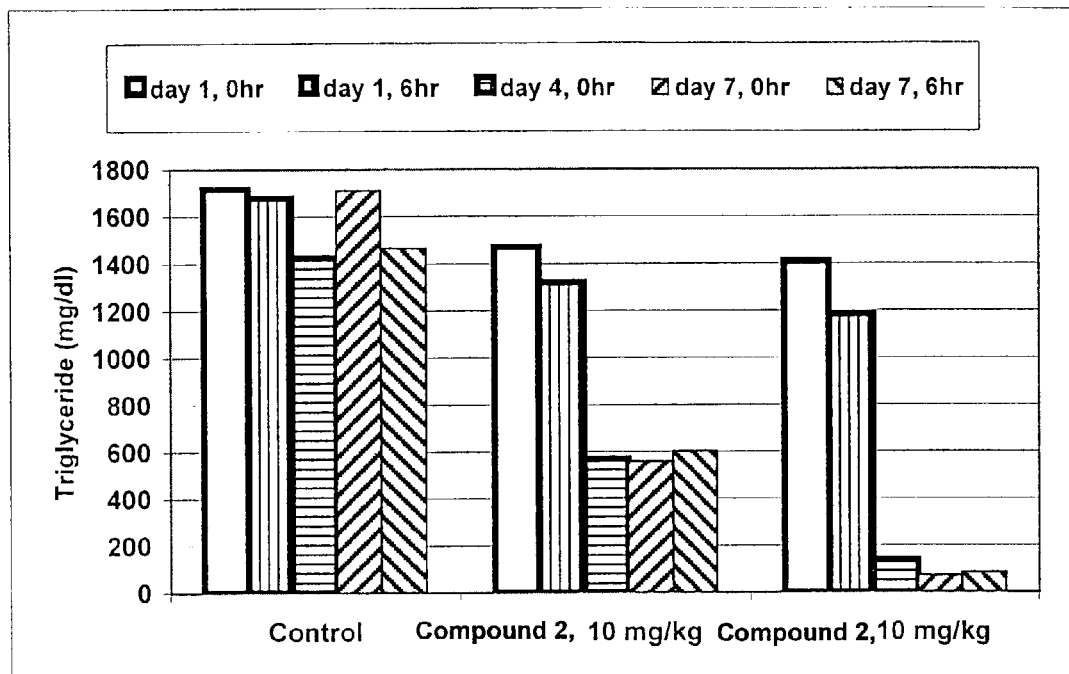
FIG. 3A shows the effect of Compound 1 and Compound 2 on serum triglyceride levels in female ZDF rats fed a diabetogenic high fat diet.
Figure 3B:
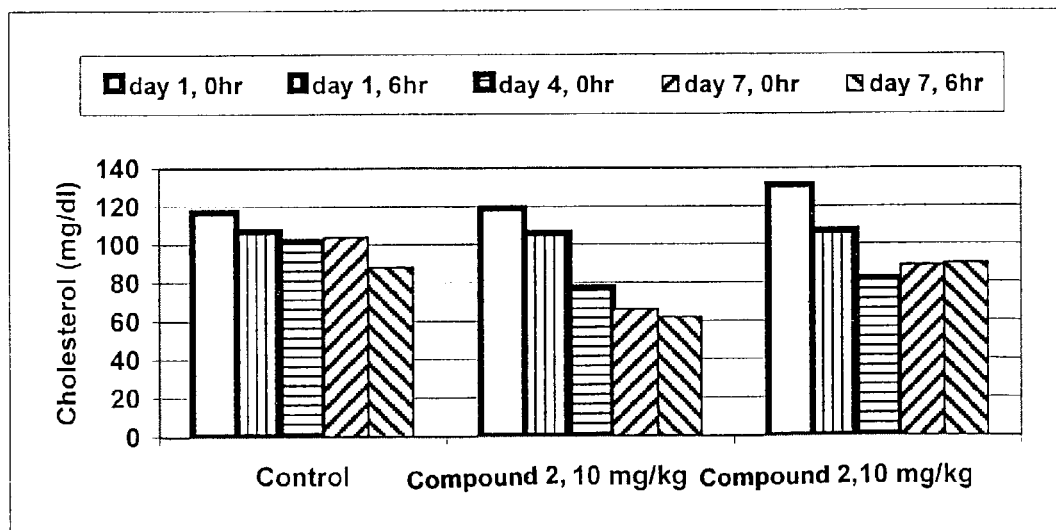
FIG. 3B shows the effect of Compound 1 and Compound 2 on serum cholesterol levels in female ZDF rats fed a diabetogenic high fat diet.

As shown in Table 2 and FIGS. 3A and 3B, Compound 1 was effective at lowering serum triglycerides. Administration of Compound 1 resulted in a decrease in serum triglycerides to about 7% of levels when compared to pre-treatment. Compound 2 also lowered serum triglycerides to about 40% of pre-treatment levels. Compound 1 and Compound 2 also exhibited a more modest effect on lowering serum cholesterol.

These results demonstrate that Compound 1 and Compound 2 is effective at lowering serum triglycerides and cholesterol. Compound 1 and Compound 2 are therefore effective treatments for lowering serum triglycerides during cardiovascular procedures such as cardiovascular surgery or angioplasty.

EXAMPLE IV

Treatment of Monkeys with an RAR Antagonist/Inhibitor

This example describes treatment of cynomologus monkeys with an RAR antagonist/inhibitor.

Five male cynomologus monkeys were employed in the study. Three of the five monkeys were treated with Compound 1 at a daily dosage of 1.25 mg/kg (orally) for a period of 25 days. Compound 1 is an RAR antagonist or inhibitor. The remaining two were similarly treated with a vehicle to serve as control. Serum samples were collected on days 1, 8, 15, 22 and 25 for triglyceride determination. Serum samples from days 8, 15, 22 and 25 were also assayed for the concentration of Compound 1. All monkeys appeared healthy throughout the study period, with no change in body weight or rate of food consumption.

A highly significant decrease of serum triglycerides was observed in each of the three monkeys receiving Compound 1 treatment (see Table 3). When compared to day 1 (baseline), the average decrease was 52%, 54% and 51% for the three monkeys treated with Compound 1, while the two control monkeys had an average increase of 48% and 89%.

The triglyceride lowering effect and the relatively high blood concentration of Compound 1 (Table 4) indicated that Compound 1 was well absorbed by monkeys when given orally.

TABLE 3

Serum triglycerides (mg/dl) of male cynomolgus monkeys treated with Compound 1 by gastric intubation.

| Compound 1 | Animal # | Day 1 | Day 8 | Day 15 | Day 22 | Day 25 |
|---|---|---|---|---|---|---|
| 0.0 mg/0.4 ml/kg | 18-18 | 45.1 | 82.2 | 92.1 | 83.8 | 82.9 |
| | 18-40 | 40.7 | 43.5 | 47.8 | 83.6 | 65.4 |
| | Mean | 42.9 | 62.9 | 70.0 | 83.7 | 74.2 |
| 1.0 mg/0.4 ml/kg | 28-199 | 48.8 | 24.3 | 18.2 | 30.4 | 20.3 |
| | 28-312 | 52.5 | 21.6 | 30.7 | 20.6 | 23.4 |
| | 28-318 | 58.5 | 19.2 | 29.6 | 36.5 | 28.3 |
| | Mean | 53.3 | 21.7 | 26.2 | 29.2 | 24.0 |

TABLE 4

Serum concentration (ng/mL) of Compound 1 in male cynomolgus monkeys treated with Comppound 1 by gastric intubation.

| COMPOUND 1 | Animal # | Day 8 | Day 15 | Day 22 | Day 25 |
|---|---|---|---|---|---|
| 0.0 mg/0.4 ml/kg | 18-18 | BLQ | 0.615 | 0.247 | 1.23 |
| | 18-40 | 0.384 | 1.5 | 0.107 | 1.23 |
| 1.0 mg/0.4 ml/kg | 28-199 | >194 | 1408 | 488 | >2878 |
| | 28-312 | 401 | 140 | 882 | 431 |
| | 28-318 | >148 | >177 | >118 | >1955 |

These results demonstrate that Compound 1 lowers serum triglycerides in monkeys at a daily dose of 1.25 mg/kg without any noticeable abnormal clinical signs.

EXAMPLE V

Effect of RAR Antagonists on Serum Triglycerides and Hepatic Triglyceride Output in Male SJL Mice This example describes the effect of treating a SJL mouse model with RAR antagonists/inhibitors on serum triglycerides.

Male SJL mice were dosed orally with vehicle, Compound 1 (an RAR pan-antagonist), or Compound 3 (an RARE antagonist) for 4 consecutive days. The structure and synthesis of Compound 1 is described in Example I. The structure of Compound 3 is shown below, and the compound was synthesized using routine methods:

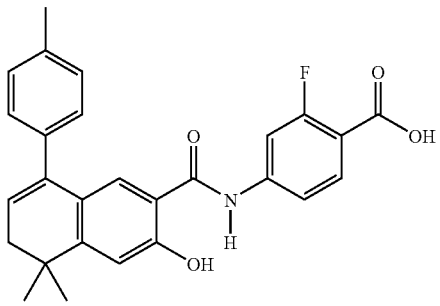

The test compounds were dissolved in corn oil and given at a dosage/volume of 20 mg/5 ml/kg.

On day 3, serum triglycerides (STG) were determined from samples collected at 7 a.m.

Figure 4:
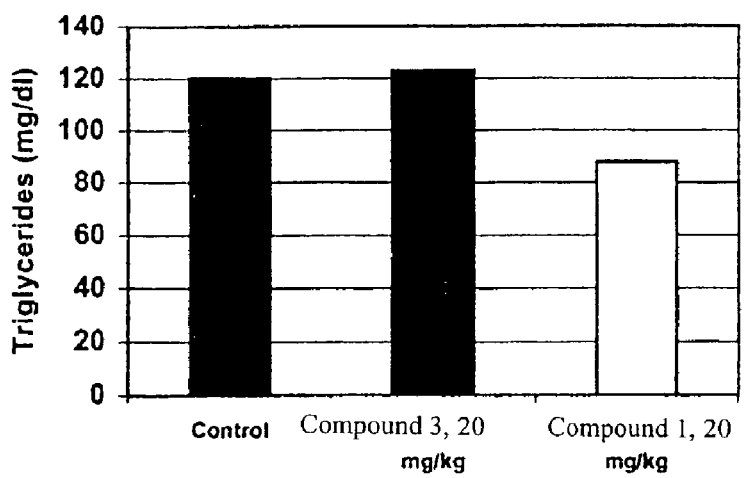
FIG. 4 shows the level of serum triglycerides in SJL mice 24 hours after 2 daily dosings (Day 3, 8 a.m.) of a control, Compound 3 or Compound 1.
Figure 5:
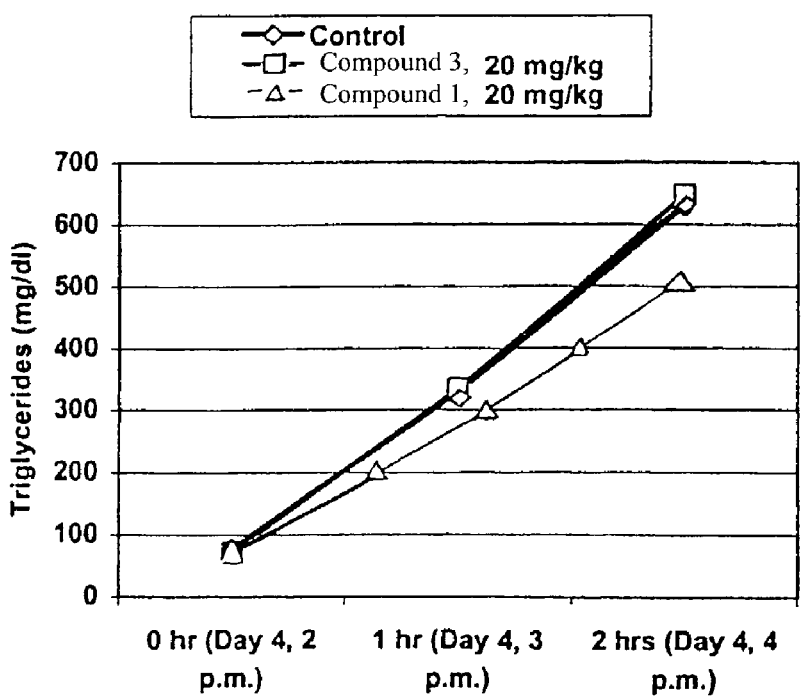
FIG. 5 shows the level of serum triglycerides of SJL male mice after 4 daily oral treatments, followed by 6 hours of fasting before WR-1339 is administered (0 hr).

On day 4, animals were fasted after dosing, starting at 8 a.m. Following 6 hours of fasting, blood samples were collected prior to intravenous injection of WR-1339 at 100 mg/5 ml/kg. Additional serum samples were collected at 1 and 2 hours after WR-1339 injection. WR-1339 is a detergent that inactivates lipoprotein lipase and thus prevents the removal of triglycerides from circulation. By measuring the increase of STG after WR-1339 administration in fasted animals, the hepatic triglyceride (HTG) output during fasting can be estimated. The results are shown in Table 5 and FIGS. 4 and 5.

TABLE 5

Serum triglycerides (Mean +/− SD) of mice 24 hours after 2 days of oral treatments (20 mg/kg/day) of Compound 3 and Compound 1.

| Treatment | Day 3, 8 a.m. |
| --- | --- |
| Vehicle (N = 10) | 120.4 +/− 36.3 mg/dl |
| Compound 3 (N = 9) | 123.0 +/− 13.3 mg/dl |
| Compound 1 (N = 10) | 92.7 +/− 24.0 mg/dl |

Compound 1 appeared to lower non-fasting STG (Day 3, 8 a.m.) but not fasting STG (Day 4, 2 p.m.). A reduction of HTG output after WR-1339 injection was observed with Compound 1. These effects were not observed with Compound 3 given orally.

The results also indicate that male SJL mouse is a suitable model for in vivo screening of retinoid effect on serum triglycerides. The effect could be detected after 2 days of dosing.

Figure 6:
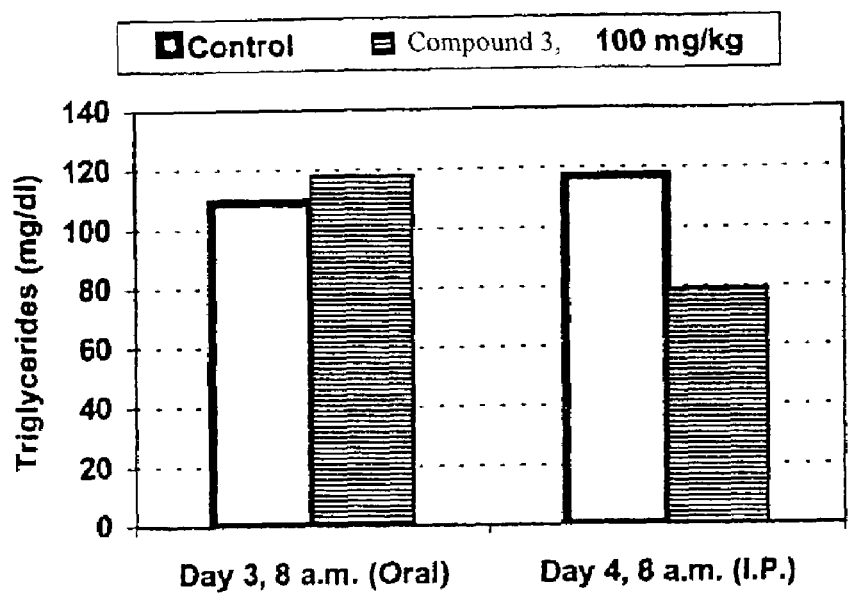
FIG. 6 shows the level of serum triglycerides of SJL mice 24 hours after two daily oral dosings (Day 3, 8 a.m.) and 16 hours after one intraperitoneal dosing (Day 4, 8 a.m.) of Compound 3.
Figure 7:
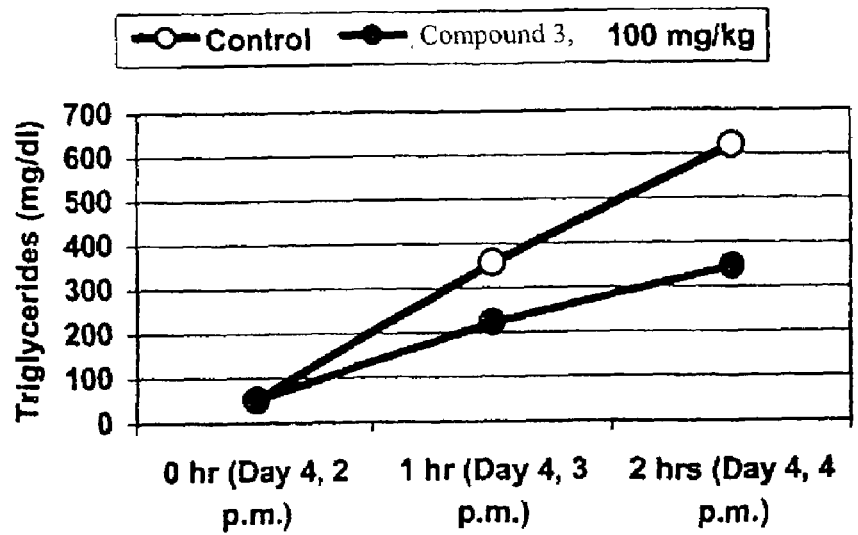
FIG. 7 shows the level of serum triglycerides of SJL mice after oral gavages and intraperitoneal injections of Compound 3, followed by 6 hours fasting before WR-1339 administration (0 hr).

Due to the lack of effect of Compound 3 at 20 mg/kg, the dose was increased to 100 mg/kg in the same set of mice. STG was determined on day 3 prior to dosing (Day 3, 8 a.m.). Again, no lowering of STG was observed (Table 5). To ensure that Compound 3 would be bioavailable, Compound 3 was dissolved in DMSO and given by intraperitoneal injections, once at 4 p.m. on day 3 and once at 8 a.m. on day 4, at a dosage of 100 mg/kg/injection. Administration of WR-1339 and blood collections on day 4 were similarly conducted as described above. The results, which are shown in Table 6 and FIGS. 6 and 7, indicate that a clear lowering of STG was observed 16 hours after a single intraperitoneal 100 mg/kg dose (Day 4, 8 a.m.). Similar to Compound 1, this effect disappeared after fasting (Day 4, 2 p.m.). HTG output was also reduced with intraperitoneal injection of Compound 3. Therefore, Compound 3 is also effective at lowering serum triglycerides, although Compound 2 may not be bioavailable when given orally to mice.

TABLE 6

Serum triglycerides (Mean +/− SD) of mice treated with Compound 3 by oral gavage (100 mg/kg) on Days 1, 2, 3 (8 a.m.) and by intraperitoneal injection (100 mg/kg) on Day 3 (4 p.m.) and 4 (8 a.m.).

| Treatment | Day 3, 8 a.m. | Day 4, 8 a.m. |
| --- | --- | --- |
| Vehicle (N = 5) | 109 +/− 39 mg/dl | 117 +/− 41 mg/dl |
| Compound 3 (N = 6) | 118 +/− 32 mg/dl | 79 +/− 33 mg/dl |

These results indicate that RAR antagonists are capable of lowering serum triglycerides in mice.

EXAMPLE VI

Treatment of New Zealand Rabbits with RAR Antagonists/Inhibitors During Cardiovascular Surgery This example describes the treatment of a New Zealand rabbit model with RAR antagonists/inhibitors.

Experiments are performed using male New Zealand rabbits (3.0 to 3.2 kg), 10 animals per group. Animals are fed a standard diet supplemented with 2% cholesterol and 6% peanut oil from 7 days prior to surgery, and the is continued for 14 days after surgery. A single daily dose of a given RAR antagonist/inhibitor, for example, Compound 1 or other RAR antagonists/inhibitors, are administered by oral gavage from 3 days before the surgery, and the dose is continued for 7 days after surgery. Control animals are fed the same diet and treated the same way except that the medium in which the RAR antagonist/inhibitor is dissolved, such as corn oil, is administered alone by oral gavage in the absence of the RAR antagonist/inhibitor.

For surgery, rabbits are anesthetized by intravenous injection of acepromazine and ketamine. The left carotid artery is exposed, and ligatures are placed at two locations, approximately 1.5 cm apart. A 27-gauge hypodermic needle is inserted into the proximal end of the segment, and a distal vent is created by a needle puncture. The arterial segment is flushed with saline, and endothelial damage is induced by filtered air infused at a rate of 240 ml/min for 5 min. Following air-drying injury, ligatures are removed, allowing re-flow to occur. The incision is closed after hemostasis is established.

Specimens are collected for determination of serum lipids and post-surgical analysis. For determining serum chemistry, blood samples are collected from the ear vein on day 13 after surgery for the analyses of serum triglycerides and cholesterol using standard protocols.

For isolation of the carotid artery for histological analysis, the animals are sacrificed on day 13 by overdosed with sodium pentobarbital. The artery from the surgical side is isolated, rinsed with saline and fixed in 10% formaline before histological processing with hematoxyline and eosin staining. About 25 histological slides are prepared from each specimen and the one with the largest intimal surface is chosen for medial and intimal surface measurements. The value serves as an indicator of myointimal thickening.

The effect of RAR antagonists on serum lipid concentrations is determined. Serum triglycerides and cholesterol of the control, untreated animals are approximately 250 and 150 mg/dl, respectively. Upon treatment with an RAR antagonist/inhibitor such as Compound 1, the serum concentration in the treated animals is expected to be lowered to about 150 and 95 mg/dl, respectively. A clear lowering of serum lipid content is directly associated with RAR antagonist/inhibitor treatment.

The effect of an RAR antagonist/inhibitor on the carotid artery is also determined following surgery. The air-drying injury induced by the surgical procedure described above results in an obvious smooth muscle cell proliferation in the intima and foamy cell infiltration in both intima and media in the artery which has been exposed to air-induced injury. However, these changes are inhibited by approximately 30 to 50% with the treatment of an RAR antagonist/inhibitor.

By lowering serum triglycerides and/or cholesterol, treatment with an RAR antagonist/inhibitor can reduce the severity of vascular inflammation after air-drying injury. Common invasive vascular procedures such as balloon and laser angioplasties also induce a similar inflammation as air-drying injury. An excessive inflammation often is a contributing factor for restenosis after the angioplastic procedures. The ability of RAR antagonists/inhibitors to inhibit inflammation will not only accelerate the process of wound healing but also reduce the incidence of restenosis. Therefore, patients who are scheduled to undergo invasive vascular procedures should benefit from the treatment of RAR antagonists prior to and after the invasive vasculare procedure.

This example demonstrates that RAR antagonists/inhibitors can be used to enhance recovery and diminish undesirable postsurgical effects of invasive vascular procedures.

All journal article, reference and patent citations provided above, in parentheses or otherwise, whether previously stated or not, are incorporated herein by reference in their entirety. Although the invention has been described with reference to the examples provided above, it is understood that various modifications can be made without departing from the spirit of the invention.

What is claimed is:

1. A method for treating vascular trauma, comprising administering to an individual undergoing vascular trauma a therapeutically effective amount of a retinoic acid receptor (RAR) antagonist represented by the following structural formula:

or a pharmaceutically acceptable salt thereof, wherein:

$R_2$ is H, F, $CF_3$ or alkoxy of 1 to 6 carbons;

$R_2^*$ is H, F or $CF_3$;

$R_8$ is H, or lower alkyl of 1 to 6 carbons;

$R_{14}$ is unsubstituted phenyl, thienyl or pyridyl, or phenyl, thienyl or pyridyl substituted with one to three $R_{15}$ groups; and $R_{15}$ is lower alkyl of 1 to 6 carbons, chlorine, $CF_3$ or alkoxy of 1 to 6 carbons.

2. The method of claim 1, wherein said vascular trauma is a surgical procedure.

3. The method of claim 2, wherein said surgical procedure is angioplasty.

4. The method of claim 1, wherein said RAR antagonist is administered prior to said surgical procedure.

5. The method of claim 4, wherein said RAR antagonist is administered about 3 to about 7 days prior to said surgical procedure.

6. The method of claim 1, wherein said RAR antagonist is administered after said surgical procedure.

7. The method of claim 6, wherein said RAR antagonist is administered at least about 7 to about 14 days after said surgical procedure.

8. The method of claim 1, wherein said administration is effective at lowering serum trigylcerides to a level at least about 20% lower than pre-treatment levels.

9. The method of claim 1, wherein said administration is effective at lowering serum triglycerides to a level at least about 50% lower than pre-treatment levels.

10. The method of claim 1, wherein:

$R_2$ is H, F, or $OCH_3$;

$R_2^*$ is H or F;

$R_{14}$ is selected from the group consisting of phenyl, 4-(lower alkyl)phenyl, 5-(lower alkyl)-2-thienyl, and 6-(lower alkyl)-3-pyridyl where lower alkyl has 1 to 6 carbons.

11. A method of for treating vascular trauma, comprising administering to an individual undergoing vascular trauma a therapeutically effective amount of a retinoic acid receptor (RAR) antagonist, wherein said RAR antagonist has the chemical structure:

or a pharmaceutically acceptable salt thereof.

12. The method of claim 1, wherein a second lipid lowering agent is administered to said individual.

13. The method of claim 12, wherein said second lipid lowering agent is a statin.

14. The method of claim 13, wherein said statin is selected from the group consisting of lovastatin, pravastatin, simvastatin, cerivastatin, fluvastatin, atorvastatin and mevastatin.

15. The method of claim 12, wherein said second lipid lowering agent is a thiazolidinedione analogue.

16. The method of claim 15, wherein said thiazolidinedione analogue is selected from troglitazone, pioglitazone and ciglitazone.

* * * * *

UNITED STATES PATENT AND TRADEMARK OFFICE
CERTIFICATE OF CORRECTION

PATENT NO. : 7,105,566 B2
APPLICATION NO. : 10/278770
DATED : September 12, 2006
INVENTOR(S) : Roshantha A. Chandraratna et al.

It is certified that error appears in the above-identified patent and that said Letters Patent is hereby corrected as shown below:

Column 29
Claim 1, line 60, delete

" 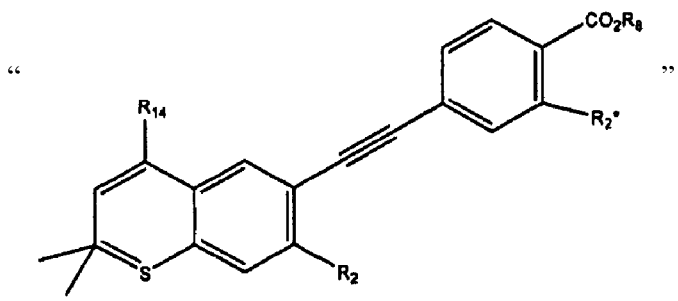 "

and insert

-- 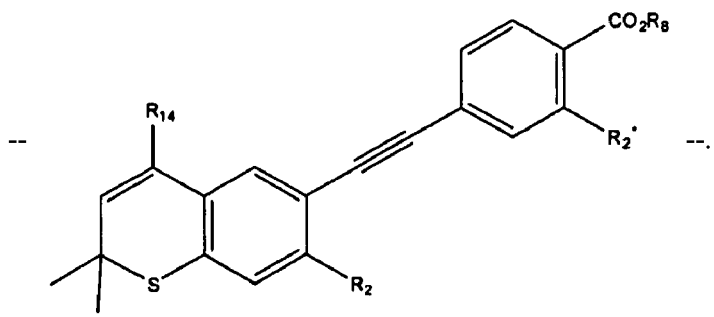 --.

UNITED STATES PATENT AND TRADEMARK OFFICE
CERTIFICATE OF CORRECTION

PATENT NO. : 7,105,566 B2
APPLICATION NO. : 10/278770
DATED : September 12, 2006
INVENTOR(S) : Roshantha A. Chandraratna et al.

It is certified that error appears in the above-identified patent and that said Letters Patent is hereby corrected as shown below:

Column 30
Claim 11, line 55, delete "

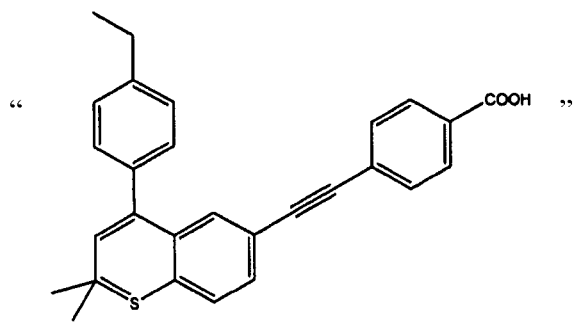

"

and insert --

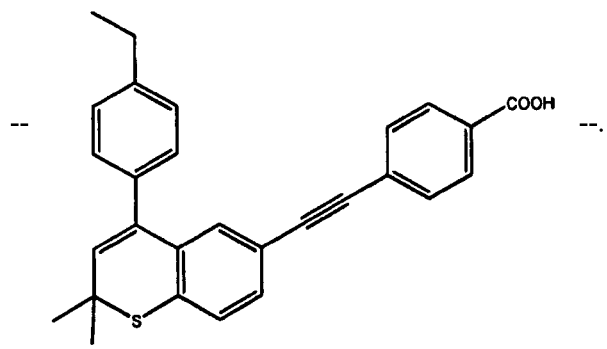

--.

Signed and Sealed this

First Day of July, 2008

JON W. DUDAS
*Director of the United States Patent and Trademark Office*